United States Patent
Stamos et al.

(10) Patent No.: US 7,087,642 B2
(45) Date of Patent: Aug. 8, 2006

(54) INHIBITORS OF IMPDH ENZYME

(75) Inventors: Dean Stamos, Framingham, MA (US);
Martin Trudeau, Tewksbury, MA (US);
Scott Bethiel, Bedford, MA (US);
Steven Ronkin, Watertown, MA (US);
Michael Badia, Bedford, MA (US);
Jeffrey Saunders, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 192 days.

(21) Appl. No.: 10/287,405

(22) Filed: Nov. 4, 2002

(65) Prior Publication Data

US 2004/0029939 A1     Feb. 12, 2004

Related U.S. Application Data

(60) Division of application No. 09/955,626, filed on Sep. 19, 2001, now Pat. No. 6,498,178, which is a continuation of application No. PCT/US00/07129, filed on Mar. 17, 2000.

(60) Provisional application No. 60/174,882, filed on Jan. 7, 2000, provisional application No. 60/125,507, filed on Mar. 19, 1999.

(51) Int. Cl.
*A61K 47/00* (2006.01)
*A61K 31/27* (2006.01)
*C07C 229/00* (2006.01)
*C07C 255/00* (2006.01)

(52) U.S. Cl. ........................ 514/476; 514/784; 514/785; 558/417; 558/414; 558/411; 560/19; 560/24; 560/27; 560/34

(58) Field of Classification Search ................ 548/567, 548/236; 549/475; 558/417, 414; 514/374, 514/227.5, 227.8, 236.8, 438, 473, 522, 476, 514/784, 785; 544/58.2, 58.5, 59, 60, 137, 544/163; 560/19, 24
See application file for complete search history.

(56) References Cited

U.S. PATENT DOCUMENTS

| | | | | |
|---|---|---|---|---|
| 5,807,876 | A * | 9/1998 | Armistead et al. | 514/374 |
| 5,932,600 | A * | 8/1999 | Saunders et al. | 514/365 |
| 6,054,472 | A * | 4/2000 | Armistead et al. | 514/374 |
| 6,128,582 | A * | 10/2000 | Wilson et al. | 702/27 |
| 6,344,465 | B1 * | 2/2002 | Armistead et al. | 514/326 |
| 6,395,763 | B1 * | 5/2002 | Stamos et al. | 514/374 |
| 6,498,178 | B1 * | 12/2002 | Stamos et al. | 514/374 |
| 6,518,291 | B1 * | 2/2003 | Saunders et al. | 514/367 |
| 6,541,496 | B1 * | 4/2003 | Armistead et al. | 514/374 |
| 6,653,309 | B1 * | 11/2003 | Saunders et al. | 514/242 |
| 6,824,769 | B1 * | 11/2004 | Chaturvedi et al. | 424/85.7 |
| 6,825,224 | B1 * | 11/2004 | Stamos et al. | 514/374 |

FOREIGN PATENT DOCUMENTS

WO    WO 97/40028    10/1997

* cited by examiner

*Primary Examiner*—Sabiha N. Qazi
(74) *Attorney, Agent, or Firm*—Michael C. Badia; Vertex Pharmaceuticals Incorporated

(57) ABSTRACT

The present invention relates to compounds which inhibit IMPDH. This invention also relates to pharmaceutical compositions comprising these compounds. The compounds and pharmaceutical compositions of this invention are particularly well suited for inhibiting IMPDH enzyme activity and consequently, may be advantageously used as therapeutic agents for IMPDH-mediated processes. This invention also relates to methods for inhibiting the activity of IMPDH using the compounds of this invention and related compounds.

28 Claims, No Drawings

INHIBITORS OF IMPDH ENZYME

CROSS-REFERENCE TO RELATED APPLICATIONS

This application is a divisional of U.S. application Ser. No. 09/955,626, filed Sep. 19, 2001, now U.S. Pat. No. 6,498,178 which is a continuation of co-pending International Application PCT/US00/07129, filed Mar. 17, 2000, which claims priority from U.S. Provisional application 60/125,507, filed Mar. 19, 1999 and U.S. Provisional application 60/174,882, filed Jan. 7, 2000.

TECHNICAL FIELD OF THE INVENTION

The present invention relates to compounds which inhibit IMPDH. This invention also relates to pharmaceutical compositions comprising these compounds. The compounds and pharmaceutical compositions of this invention are particularly well suited for inhibiting IMPDH enzyme activity and consequently, may be advantageously used as therapeutic agents for IMPDH-mediated processes. This invention also relates to methods for inhibiting the activity of IMPDH using the compounds of this invention and related compounds.

BACKGROUND OF THE INVENTION

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH; EC 1.1.1.205) is an enzyme involved in the de novo synthesis of guanine nucleotides. IMPDH catalyzes the NAD-dependent oxidation of inosine-5'-monophosphate (IMP) to xanthosine-5'-monophosphate (XMP)[Jackson R. C. et. al., Nature, 256, pp. 331–333, (1975)].

IMPDH is ubiquitous in eukaryotes, bacteria and protozoa [Y. Natsumeda & S. F. Carr, Ann. N.Y. Acad., 696, pp. 88–93 (1993)]. The prokaryotic forms share 30–40% sequence identity with the human enzyme. Two isoforms of human IMPDH, designated type I and type II, have been identified and sequenced [F. R. Collart and E. Huberman, J. Biol. Chem., 263, pp. 15769–15772, (1988); Y. Natsumeda et. al., J. Biol. Chem., 265, pp. 5292–5295, (1990)]. Each is 514 amino acids, and they share 84% sequence identity. Both IMPDH type I and type II form active tetramers in solution, with subunit molecular weights of 56 kDa [Y. Yamada et. al., Biochemistry, 27, pp. 2737–2745 (1988)].

The de novo synthesis of guanosine nucleotides, and thus the activity of IMPDH, is particularly important in B and T-lymphocytes. These cells depend on the de novo, rather than salvage pathway to generate sufficient levels of nucleotides necessary to initiate a proliferative response to mitogen or antigen [A. C. Allison et. al., Lancet II, 1179, (1975) and A. C. Allison et. al., Ciba Found. Symp., 48, 207, (1977)]. Thus, IMPDH is an attractive target for selectively inhibiting the immune system without also inhibiting the proliferation of other cells.

Immunosuppression has been achieved by inhibiting a variety of enzymes including for example, the phosphatase calcineurin (inhibited by cyclosporin and FK-506); dihydroorotate dehydrogenase, an enzyme involved in the biosynthesis of pyrimidines (inhibited by leflunomide and brequinar); the kinase FRAP (inhibited by rapamycin); and the heat shock protein hsp70 (inhibited by deoxyspergualin). [See B. D. Kahan, Immunological Reviews, 136, pp. 29–49 (1993); R. E. Morris, The Journal of Heart and Lung Transplantation, 12(6), pp. S275–S286 (1993)].

Inhibitors of IMPDH are also known. U.S. Pat. Nos. 5,380,879 and 5,444,072 and PCT publications WO 94/01105 and WO 94/12184 describe mycophenolic acid (MPA) and some of its derivatives as potent, uncompetitive, reversible inhibitors of human IMPDH type I ($K_i$=33 nM) and type II ($K_i$=9 nM). MPA has been demonstrated to block the response of B and T-cells to mitogen or antigen [A. C. Allison et. al., Ann. N.Y. Acad. Sci., 696, 63, (1993).

Immunosuppressants, such as MPA, are useful drugs in the treatment of transplant rejection and autoimmune diseases. [R. E. Morris, Kidney Intl., 49, Suppl. 53, S-26, (1996)]. However, MPA is characterized by undesirable pharmacological properties, such as gastrointestinal toxicity. [L. M. Shaw, et. al., Therapeutic Drug Monitoring, 17, pp. 690–699, (1995)].

Nucleoside analogs such as tiazofurin, ribavirin and mizoribine also inhibit IMPDH [L. Hedstrom, et. al. Biochemistry, 29, pp. 849–854 (1990)]. These compounds, however, suffer from lack of specificity to IMPDH.

Mycophenolate mofetil, a prodrug which quickly liberates free MPA in vivo, was recently approved to prevent acute renal allograft rejection following kidney transplantation. [L. M. Shaw, et. al., Therapeutic Drug Monitoring, 17, pp. 690–699, (1995); H. W. Sollinger, Transplantation, 60, pp. 225–232 (1995)]. Several clinical observations, however, limit the therapeutic potential of this drug. [L. M. Shaw, et. al., Therapeutic Drug Monitoring, 17, pp. 690–699, (1995)]. MPA is rapidly metabolized to the inactive glucuronide in vivo. [A. C. Allison and E. M. Eugui, Immunological Reviews, 136, pp. 5–28 (1993)]. The glucuronide then undergoes enterohepatic recycling causing accumulation of MPA in the gastrointestinal tract where it cannot exert its IMPDH inhibitory activity on the immune system. This effectively lowers the drug's in vivo potency, while increasing its undesirable gastrointestinal side effects.

More recently, IMPDH inhibitors of different classes have been described in PCT publications WO 97/40028 and WO 98/40381.

It is also known that IMPDH plays a role in other metabolic events. Increased IMPDH activity has been observed in rapidly proliferating human leukemic cell lines and other tumor cell lines, indicating IMPDH as a target for anti-cancer as well as immunosuppressive chemotherapy [M. Nagai et. al., Cancer Res., 51, pp. 3886–3890, (1991)]. IMPDH has also been shown to play a role in the proliferation of smooth muscle cells, indicating that inhibitors of IMPDH, such as MPA or rapamycin, may be useful in preventing restenosis or other hyperproliferative vascular diseases [C. R. Gregory et al., Transplantation, 59, pp. 655–61 (1995); PCT publication WO 94/12184; and PCT publication WO 94/01105].

Additionally, IMPDH has been shown to play a role in viral replication in some virus-infected cell lines. [S. F. Carr, J. Biol. Chem., 268, pp. 27286–27290 (1993)]. Analogous to lymphocytes and lymphocytic and tumor cell lines, the implication is that the de novo, rather than the salvage, pathway is critical in the process of viral replication.

Thus, there remains a need for potent IMPDH inhibitors with improved pharmacological properties. Such inhibitors would have therapeutic potential as immunosuppressants, anti-cancer agents, anti-vascular hyperproliferative agents, anti-inflammatory agents, antifungal agents, antipsoriatic and anti-viral agents.

SUMMARY OF THE INVENTION

The present invention provides compounds, and pharmaceutically acceptable derivatives thereof, that are useful as inhibitors of IMPDH. The compounds of this invention can be used alone or in combination with other therapeutic or prophylactic agents, such as anti-virals, anti-inflammatory agents, antibiotics, and immunosuppressants for the treatment or prophylaxis of transplant rejection and autoimmune disease.

Additionally, these compounds are useful, alone or in combination with other agents, as therapeutic and prophylactic agents for antiviral, anti-tumor, anti-cancer, anti-inflammatory agents, antifungal agents, antipsoriatic immunosuppressive chemotherapy and restenosis therapy regimens.

The invention also provides pharmaceutical compositions comprising the compounds of this invention, as well as multi-component compositions comprising additional IMPDH compounds together with an immunosuppressant. The invention also provides methods of using the compounds of this invention, as well as other related compounds, for the inhibition of IMPDH.

DETAILED DESCRIPTION OF THE INVENTION

In order that the invention herein described may be more fully understood, the following detailed description is set forth. In the description, the following abbreviations are used:

| Designation | Reagent or Fragment |
| --- | --- |
| Ac | acetyl |
| Me | methyl |
| Et | ethyl |
| Bn | benzyl |
| CDI | carbonyldiimidazole |
| DBU | 1,8-diazabicyclo[5.4.0]undec-7-ene |
| DIEA | diisopropylethylamine |
| DMAP | dimethylaminopyridine |
| DMF | dimethylformamide |
| DMSO | dimethylsulfoxide |
| DPPA | diphenyl phosphoryl acid |
| EDC | 1-(3-dimethylaminopropyl)-3-ethylcarbodiimide hydrochloride |
| EtOAc | ethyl acetate |
| IPA | isopropyl alcohol |
| MeCN | acetonitrile |
| THF | tetrahydrofuran |
| TEA | triethylamine |
| t-bu | tert-butyl |
| BOC | butyloxycarbonyl |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The terms "halo" or "halogen" refer to a radical of fluorine, chlorine, bromine or iodine.

The term "immunosuppressant" refers to a compound or drug which possesses immune response inhibitory activity. Examples of such agents include cyclosporin A, FK506, rapamycin, leflunomide, deoxyspergualin, prednisone, azathioprine, mycophenolate mofetil, OKT3, ATAG, interferon and mizoribine.

The term "interferon" refers to all forms of interferons, including but not limited to alpha, beta and gamma forms.

IMPDH-mediated disease refers to any disease state in which the IMPDH enzyme plays a regulatory role in the metabolic pathway of that disease. Examples of IMPDH-mediated disease include transplant rejection and autoimmune diseases, such as rheumatoid arthritis, multiple sclerosis, juvenile diabetes, asthma, and inflammatory bowel disease, as well as inflammatory diseases, cancer, viral replication diseases and vascular diseases.

For example, the compounds, compositions and methods of using them of this invention may be used in the treatment of transplant rejection (e.g., kidney, liver, heart, lung, pancreas (islet cells), bone marrow, cornea, small bowel and skin allografts and heart valve xenografts), rheumatoid arthritis, multiple sclerosis, juvenile diabetes, asthma, inflammatory bowel disease (Crohn's disease, ulcerative colitis), lupus, diabetes mellitus, myasthenia gravis, psoriasis, dermatitis, eczema, seborrhea, pulmonary inflammation, eye uveitis, hepatitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, and glomerulonephritis, scleroderma, lichen planus, viteligo (depigmentation of the skin), autoimmune thyroiditis, and alveolitis, inflammatory diseases such as osteoarthritis, acute pancreatitis, chronic pancreatitis, asthma and adult respiratory distress syndrome, as well as in the treatment of cancer and tumors, such as solid tumors, lymphomas and leukemia, vascular diseases, such as restenosis, stenosis and atherosclerosis, and DNA and RNA viral replication diseases, such as retroviral diseases, and herpes.

Additionally, IMPDH enzymes are also known to be present in bacteria and thus may regulate bacterial growth. As such, the IMPDH-inhibitor compounds, compositions and methods described herein may be useful in treatment or prevention of bacterial infection, alone or in combination with other antibiotic agents.

The term "treating" as used herein refers to the alleviation of symptoms of a particular disorder in a patient or the improvement of an ascertainable measurement associated with a particular disorder. As used herein, the term "patient" refers to a mammal, including a human.

The terms "HBV", "HCV" and "HGV" refer to hepatitis-B virus, hepatitis-C virus and hepatitis-G virus, respectively.

According to one embodiment, the invention provides compounds of formula A:

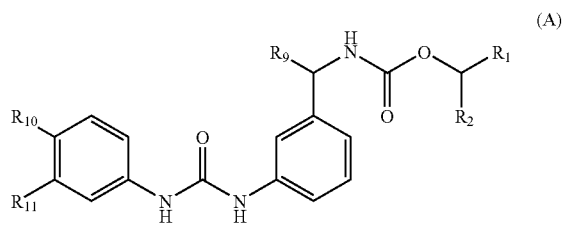

(A)

wherein:
  each of $R_1$ and $R_2$ is independently selected from hydrogen; —$CF_3$; —($C_1$–$C_6$)-straight or branched alkyl;

—($C_2$–$C_6$)-straight or branched alkenyl or alkynyl; —($C_1$–$C_6$)-straight or branched alkyl-$R_7$; -[($C_2$–$C_6$)-straight or branched alkenyl or alkynyl]-$R_7$ or —$R_7$; and wherein at least one of $R_1$ or $R_2$ is —($C_1$–$C_6$)-straight or branched alkyl-$R_7$; -[($C_2$–$C_6$)-straight or branched alkenyl or alkynyl]-$R_7$ or —$R_7$ wherein up to 4 hydrogen atoms in any of said alkyl, alkenyl or alkynyl are optionally and independently replaced by $R_3$; or wherein $R_1$ and $R_2$ are alternatively taken together to form tetrahydrofuranyl, wherein when $R_9$ is hydrogen, (R)-methyl, (R)-ethyl or (R)-hydroxymethyl, one hydrogen atom in said tetrahydrofuran is replaced by —$OR_6$ or —$R_7$, and wherein when $R_9$ is (S)-methyl, (S)-ethyl or (S)-hydroxymethyl, one hydrogen atom in said tetrahydrofuran is optionally replaced by —$OR_6$ or —$R_7$;

wherein when $R_9$ is hydrogen, (R)-methyl, (R)-ethyl or (R)-hydroxymethyl and each of $R_1$ and $R_2$ are independently hydrogen, unsubstituted —($C_1$–$C_6$)-straight or branched alkyl, or unsubstituted —($C_2$–$C_6$)-straight or branched alkenyl or alkynyl, then the portion of the compound represented by —CH($R_1$)$R_2$ is a $C_5$–$C_{12}$ straight or branched alkyl, alkenyl or alkynyl;

each $R_3$ is independently selected from halo, CN, —$OR_4$, or —N($R_5$)$_2$;

$R_4$ is selected from hydrogen, —($C_1$–$C_6$)-straight or branched alkyl, —($C_2$–$C_6$)-straight or branched alkenyl or alkynyl, -[($C_1$–$C_6$)-straight or branched alkyl]-$R_7$, -[($C_2$–$C_6$)-straight or branched alkenyl or alkynyl]-$R_7$, —C(O)-[($C_1$–$C_6$)-straight or branched alkyl], —C(O)-[($C_2$–$C_6$)-straight or branched alkenyl or alkynyl], —C(O)-[($C_1$–$C_6$)-straight or branched alkyl]-N($R_8$)$_2$, —C(O)—[($C_2$–$C_6$)-straight or branched alkenyl or alkynyl]-N($R_8$)$_2$, —P(O)(O$R_8$)$_2$, —P(O)(O$R_8$)($R_8$), —C(O)—$R_7$, -[($C_1$–$C_6$)-straight or branched alkyl]-CN, —S(O)$_2$N($R_5$)$_2$ or -[($C_2$–$C_6$)-straight or branched alkenyl or alkynyl]-CN;

each $R_5$ is independently selected from hydrogen, —($C_1$–$C_6$)-straight or branched alkyl, —($C_2$–$C_6$)-straight or branched alkenyl or alkynyl, -[($C_1$–$C_6$)-straight or branched alkyl]-$R_7$, -[($C_2$–$C_6$)-straight or branched alkenyl or alkynyl]-$R_7$, -[($C_1$–$C_6$)-straight or branched alkyl]-CN, -[($C_2$–$C_6$)-straight or branched alkenyl or alkynyl]-CN, -[($C_1$–$C_6$)-straight or branched alkyl]-$OR_4$, -[($C_2$–$C_6$)-straight or branched alkenyl or alkynyl]-$OR_4$, —C(O)—($C_1$–$C_6$)-straight or branched alkyl, —C(O)-[($C_2$–$C_6$)-straight or branched alkenyl or alkynyl], —C(O)—$R_7$, —C(O)O—$R_7$, —C(O)O—($C_1$–$C_6$)-straight or branched alkyl, —C(O)O-[($C_2$–$C_6$)-straight or branched alkenyl or alkynyl], —S(O)$_2$—($C_1$–$C_6$)-straight or branched alkyl, or —S(O)$_2$—$R_7$; or two $R_5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or S(O)$_2$;

$R_6$ is selected from —C(O)—CH$_3$, —CH$_2$—C(O)—OH, —CH$_2$—C(O)—O-tBu, —CH$_2$—CN, or —CH$_2$—C≡CH;

each $R_7$ is a monocyclic or bicyclic ring system wherein in said ring system:
  i. each ring comprises 3 to 7 ring atoms independently selected from C, N, O or S;
  ii. no more than 4 ring atoms are selected from N, O or S;
  iii. any CH$_2$ is optionally replaced with C(O);
  iv. any S is optionally replaced with S(O) or S(O)$_2$;

each $R_8$ is independently selected from hydrogen or -[$C_1$–$C_4$]-straight or branched alkyl;

wherein in any ring system in said compound up to 3 hydrogen atoms bound to the ring atoms are optionally and independently replaced with halo, hydroxy, nitro, cyano, amino, ($C_1$–$C_4$)-straight or branched alkyl; O—($C_1$–$C_4$)-straight or branched alkyl, ($C_2$–$C_4$)-straight or branched alkenyl or alkynyl, or O—($C_2$–$C_4$)-straight or branched alkenyl or alkynyl; and wherein any ring system is optionally benzofused;

$R_9$ is selected from hydrogen, (R)-methyl, (S)-methyl, (R)-ethyl, (S)-ethyl, (R)-hydroxymethyl or (S)-hydroxymethyl;

$R_{10}$ is selected from —C≡N or 5-oxazolyl; and $R_{11}$ is selected from halo, —O—($C_1$–$C_3$) straight alkyl, or —O—($C_2$–$C_3$) straight alkenyl or alkynyl.

Also within the scope of formula (A) are prodrugs, which are formed by esterifying either or both of $R_1$ or $R_2$. Examples of such prodrugs are compounds 143 to 156 in Table 1, set forth below.

The term "monocyclic ring system", as used herein, includes saturated, partially unsaturated and fully unsaturated ring structures. The term "bicyclic ring system", as used herein, includes systems wherein each ring is independently saturated, partially unsaturated and fully unsaturated. Examples of monocyclic and bicyclic ring systems useful in the compounds of this invention include, but are not limited to, cyclopentane, cyclopentene, indane, indene, cyclohexane, cyclohexene, cyclohexadiene, benzene, tetrahydronaphthalene, decahydronaphthalene, naphthalene, pyridine, piperidine, pyridazine, pyrimidine, pyrazine, 1,2,3-triazine, 1,2,4-triazine, 1,3,5-triazine, 1,2,3,4-tetrazine, 1,2,4,5-tetrazine, 1,2,3,4-tetrahydroquinoline, quinoline, 1,2,3,4-tetrahydroisoquinoline, isoquinoline, cinnoline, phthalazine, quinazoline, quinoxaline, 1,5-naphthyridine, 1,6-naphthyridine, 1,7-naphthyridine, 1,8-naphthyridine, 2,6-naphthyridine, 2,7-naphthyridine, pteridine, acridine, phenazine, 1,10-phenatroline, dibenzopyrans, 1-benzopyrans, phenothiazine, phenoxazine, thianthrene, dibenzo-p-dioxin, phenoxathiin, phenoxthionine, morpholine, thiomorpholine, tetrahydropyan, pyran, benzopyran, 1,4-dioxane, 1,3-dioxane, dihyropyridine, dihydropyran, 1-pyrindine, quinuclidine, triazolopyridine, β-carboline, indolizine, quinolizidine, tetrahydronaphtheridine, diazaphenanthrenes, thiopyran, tetrahydrothiopyran, benzodioxane, furan, benzofuran, tetrahydrofuran, pyrrole, indole, thiophene, benzothiopene, carbazole, pyrrolidine, pyrazole, isoxazole, isothiazole, imidazole, oxazole, thiazole, 1,2,3-triazole, 1,2,4-triazole, 1,2,3-oxadiazole, 1,2,4-oxadiazole, 1,3,4 oxadiazole, 1,2,5-oxadiazole, 1,2,3-thiadiazole, 1,2,4-thiadiazole, 1,3,4-thiadiazole, 1,2,5 thiadiazole, tetrazole, benzothiazole, benzoxazole, benzotriazole, benzimidazole, benzopyrazole, benzisothiazole, benzisoxazole and purine.

Additional monocyclic and bicyclic structures falling within the above description may be found in A. R. Katritzky, and C. W. Rees, eds. "*Comprehensive Heterocyclic Chemistry: Structure, Reactions, Synthesis and Use of Heterocyclic Compounds, Vol. 1–8,*" Pergamon Press, NY (1984), the disclosure of which is herein incorporated by reference.

It should be understood that heterocycles may be attached to the rest of the compound by any atom of the heterocycle which results in the creation of a stable structure.

The term "ring atom", as used herein, refers to a backbone atom that makes up the ring. Such ring atoms are selected from C, N, O or S and are bound to 2 or 3 other such ring atoms (3 in the case of certain ring atoms in a bicyclic ring system). The term "ring atom" does not include hydrogen.

The terms "-[($C_1$–$C_6$)-straight or branched alkyl]-X" and "-[($C_2$–$C_6$)-straight or branched alkenyl or alkynyl]-X", wherein X is anything indicated as being bound to the alkyl, alkenyl or alkynyl, denotes that one or more X groups may be attached to the alkyl, alkenyl or alkynyl chain at any termini.

According to one preferred embodiment, the compound has the formula (I):

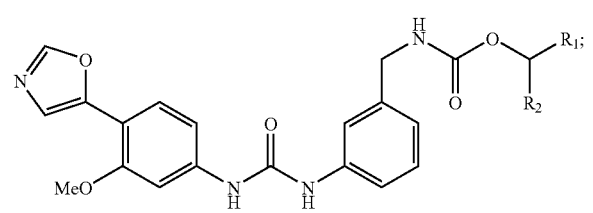

(I)

wherein
$R_1$ and $R_2$ are as defined above, or formula (IA):

(IA)

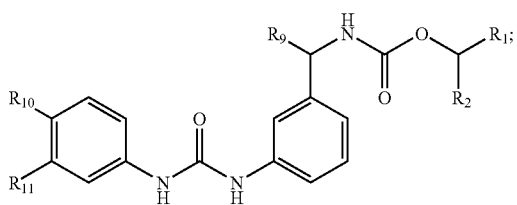

wherein
$R_9$ is selected from (R)-methyl, (S)-methyl, (R)-ethyl, (S)-ethyl, (R)-hydroxymethyl or (S)-hydroxymethyl; and
$R_1$, $R_2$, $R_{10}$ and $R_{11}$ are as defined above.

According to a more preferred embodiment of formula IA, $R_9$ is selected from (S)-methyl, (S)-ethyl, or (S)-hydroxymethyl methyl. Most preferably, $R_9$ is (S)-methyl. Compounds wherein $R_9$ is selected from (S)-methyl, (S)-ethyl, or (S)-hydroxymethyl methyl and wherein the portion of the compound represented by —CH($R_1$)$R_2$ is a $C_1$–$C_4$ straight or branched alkyl, or a $C_2$–$C_4$ straight or branched alkenyl or alkynyl fall within the genus of compounds described in WO 97/40028. However, applicants have discovered that the presence of an (S) oriented moiety at $R_9$ imparts surprising and unexpectedly increased IMPDH inhibitory activity.

According to another preferred embodiment of formula IA, $R_{11}$ is selected from O-methyl, O-ethyl or O-isopropyl.

According to a more preferred embodiment of formulae (I) and (IA), at least one of $R_1$ or $R_2$ is selected from hydrogen, methyl, ethyl, n-propyl, isopropyl, n-butyl, t-butyl, n-pentyl, phenyl, pyridyl, —$CH_2OCH_3$, —$CH_2CN$, —$CH_2OCH_2CH_2CN$, —$CH_2C(CH_3)_2CH_2CH_2CN$, —$CH_2C(CH_2CH_3)_2CH_2CH_2CN$, —$CH_2CH_2CN$, —$CH_2N(CH_2CH_2CN)_2$, —$CH_2N(CH_3)CH_2CH_2CN$, —$CH(NH_2)CH_2CN$, —$CH_2Cl$, —$CH_2OH$, —$CH_2CH_2OH$, —$CH_2CH_2OH$, —$CH_2CH_2CH_2CH_2OH$, —$CH_2CH_2OC(O)CH_3$, —$CH_2CH_2OC(O)CH_2NH_2$, —$CH_2CH_2NHCH_3$, —$CH_2CH_2N(CH_3)_2$, —$CH_2CH_2N(CH_2CH_3)_2$, —$CH_2N(CH_2CH_3)_2$, —$CH_2CH_2CH_2N(CH_3)_2$, —$CH_2CH_2CH_2N^+(CH_3)_3$, —$CH_2OCH_2CH(CH_3)_2$, —$CH_2CH_2N(CH_3)C(O)OC(CH_3)_3$, —$CH_2N(CH_2CH_2CN)CH_2CH(CH_3)_2$, —$CH(CH_2CN)N(CH_3)_2$, —$CH_2CH(CH_2CN)NHC(O)OC(CH_3)_3$, wherein n is 0 or 1.

According to an even more preferred embodiment of formula IA, one of $R_1$ or $R_2$ is selected from hydrogen, ethyl or phenyl; and the other of $R_1$ or $R_2$ is selected from —$CH_2OH$, —$CH_2CN$, —$CH_2CH_2CN$ or $CH_2N(CH_2CH_3)_2$; or $R_1$ and $R_2$ are taken together to form a 3-tetrahydrofuranyl moiety.

According to an alternate preferred embodiment of formula I, $R_1$ and $R_2$ are taken together to form a 3-tetrahydrofuranyl moiety that is substituted by —$OR_6$.

According to another preferred embodiment, the compound of formula A is selected from any of those set forth in Table 1, below.

TABLE 1
Compounds.
1 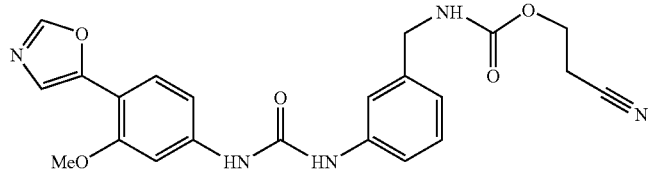
2 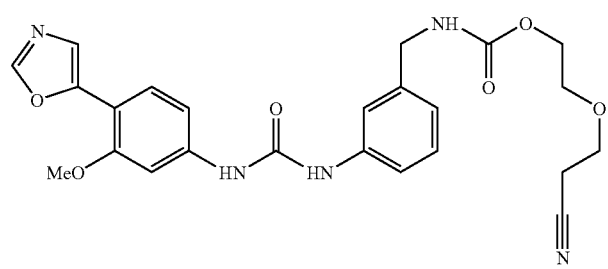
3 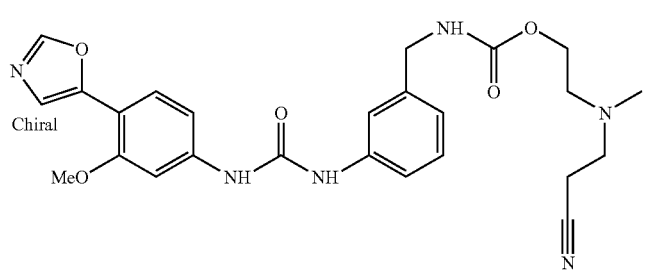
4 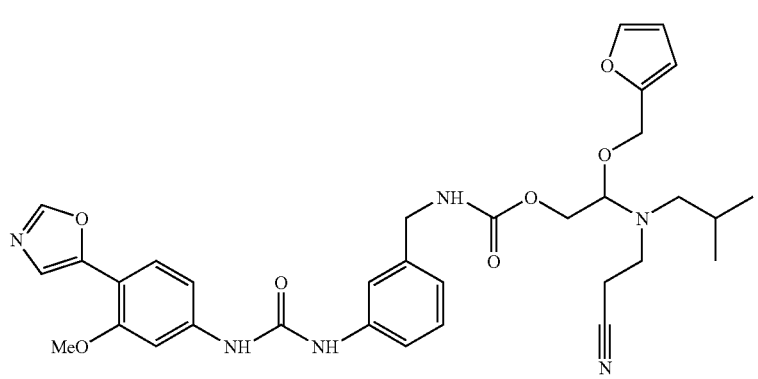
5 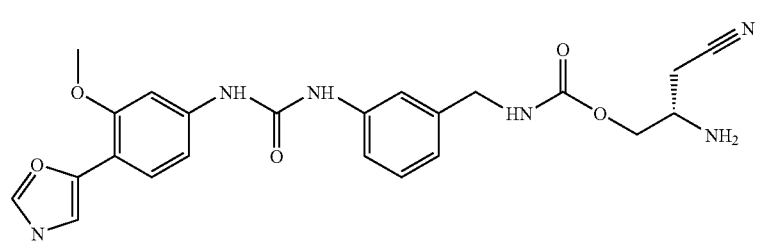
6 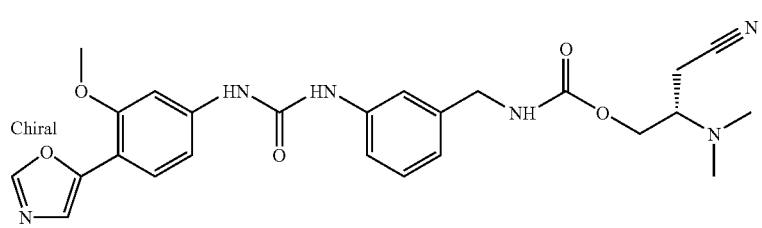

TABLE 1-continued

Compounds.

| | |
|---|---|
| 7 | (chemical structure) |
| 8 | (chemical structure) |
| 9 | (chemical structure) |
| 10 | (chemical structure) |
| 11 | (chemical structure) |
| 12 | (chemical structure) |

TABLE 1-continued
Compounds.
13 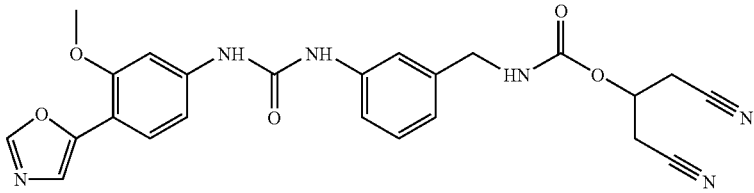
14 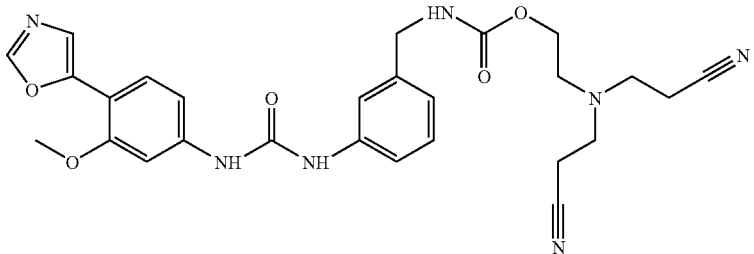
15 Chiral 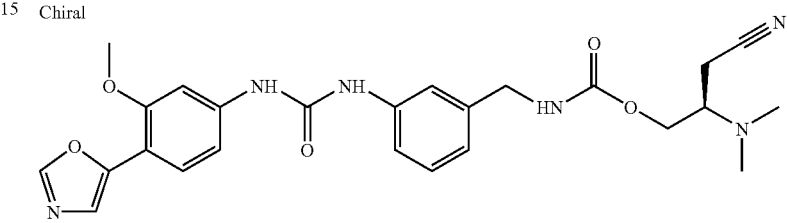
16 Chiral 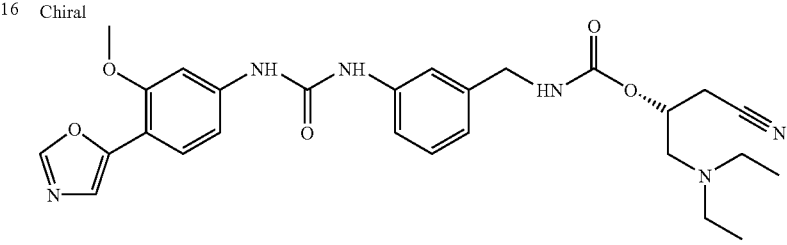
17 Chiral 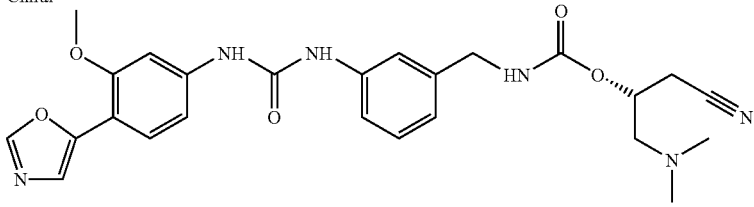
18 Chiral 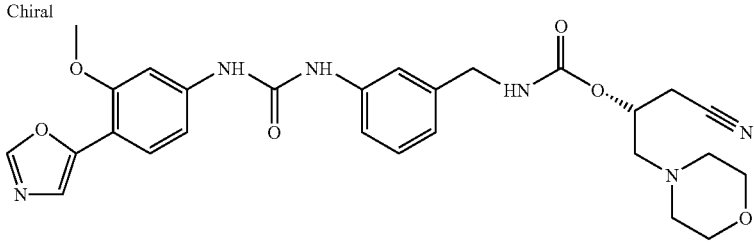

TABLE 1-continued
Compounds.
19 Chiral
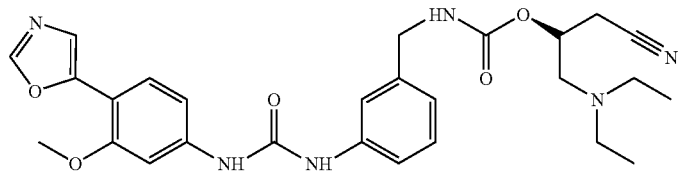
20 Chiral
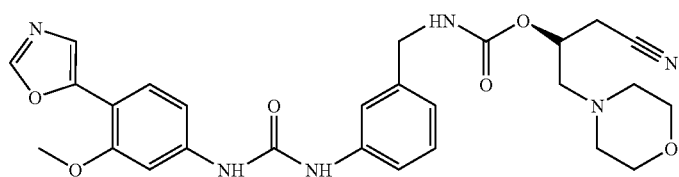
21 Chiral
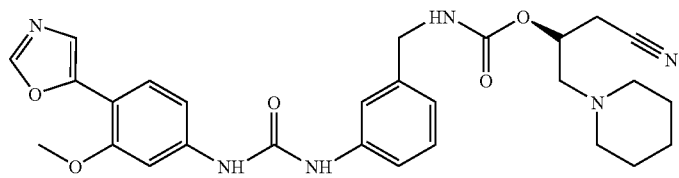
22
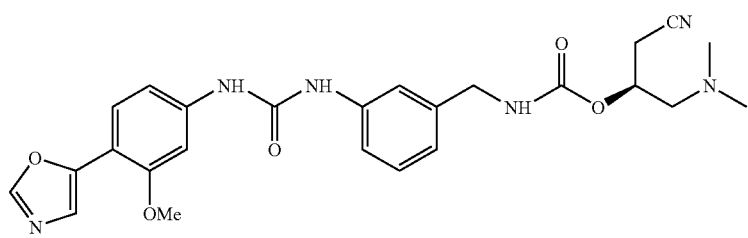
23 Chiral
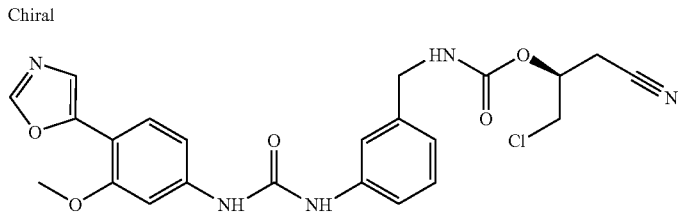
24
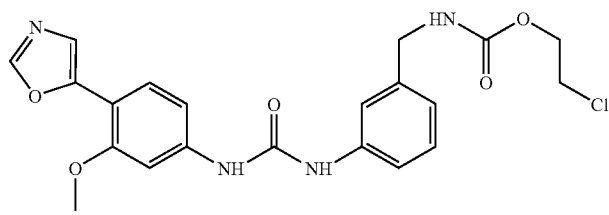

TABLE 1-continued
Compounds.
25 Chiral
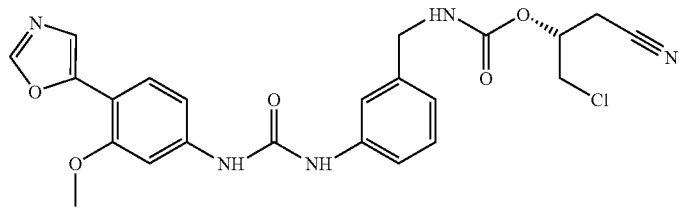
26
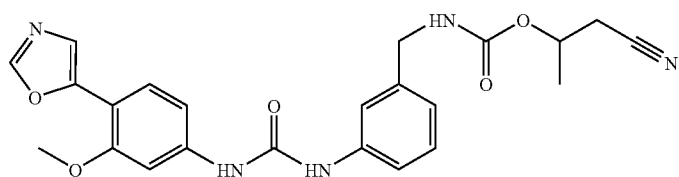
27
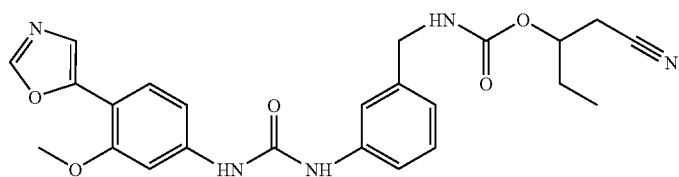
28
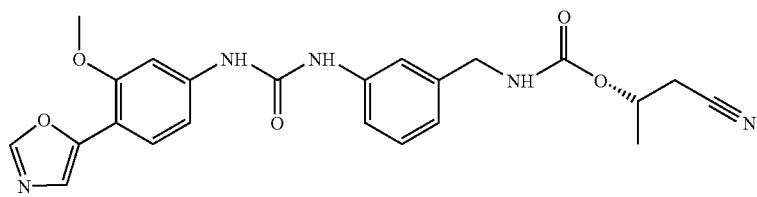
Chiral
29
Chiral
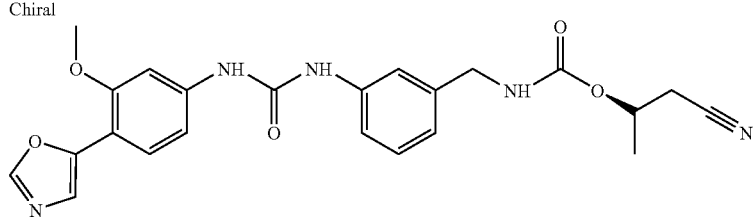
30
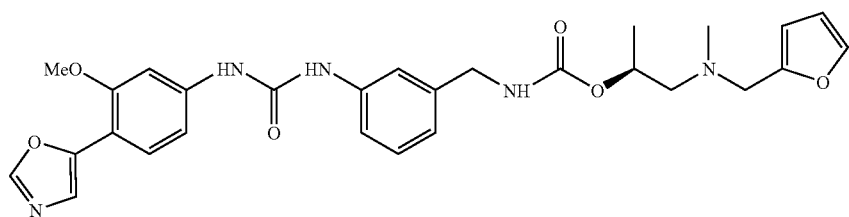

TABLE 1-continued
Compounds.
31 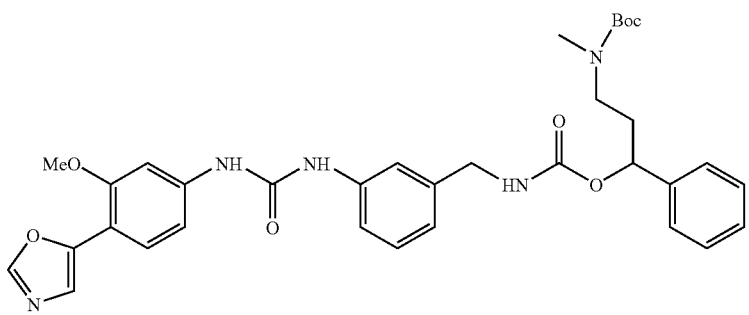
32 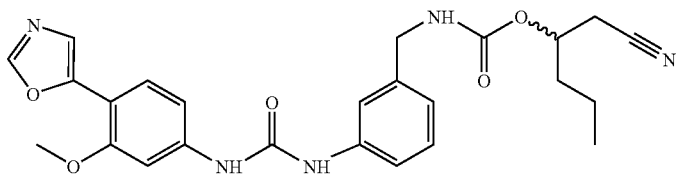
33 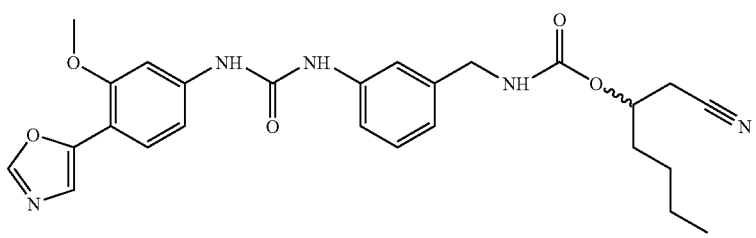
34 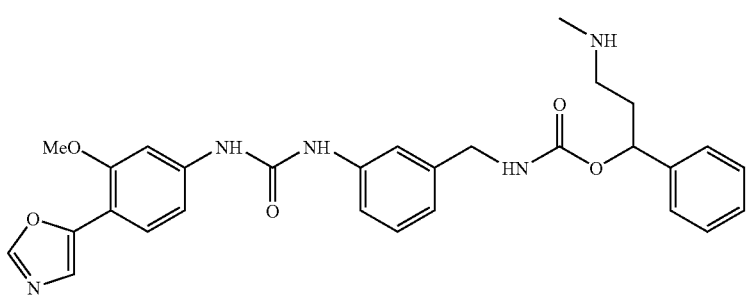
35 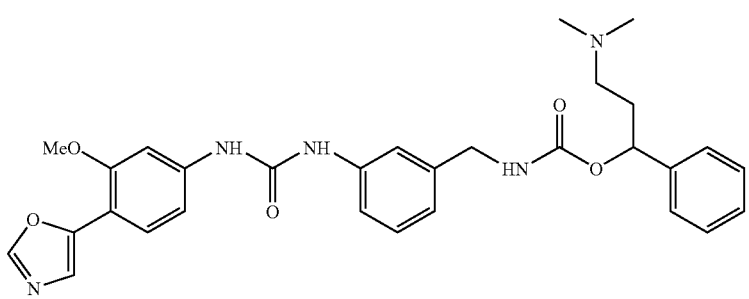

TABLE 1-continued

Compounds.

36

37

38

39

40

41

TABLE 1-continued

Compounds.

42 — [structure: 3-methoxy-4-(oxazol-5-yl)phenyl urea linked to 3-(aminomethyl)phenyl carbamate of 1-(methoxymethyl)propyl]

43 — [structure: 2-methoxy-4-(urea)-(oxazol-5-yl)phenyl linked via urea to 3-(aminomethyl)phenyl carbamate of 1-ethyl-3-hydroxypropyl]

44 — [structure: 2-methoxy-4-(urea)-(oxazol-5-yl)phenyl urea linked to 3-(aminomethyl)phenyl carbamate of 1-ethyl-4-hydroxybutyl]

45 — [structure: 3-methoxy-4-(oxazol-5-yl)phenyl urea linked to 3-(aminomethyl)phenyl carbamate of 1-(2-cyanoethyl)-3-hydroxypropyl]

46 — [structure: 3-methoxy-4-(oxazol-5-yl)phenyl urea linked to 3-(aminomethyl)phenyl carbamate of 1-(cyanomethyl)-2,2-dimethylpropyl]

47 Chiral — [structure: 3-methoxy-4-(oxazol-5-yl)phenyl urea linked to 3-(aminomethyl)phenyl carbamate of (R)-1-methyl-3-cyanopropyl]

TABLE 1-continued
Compounds.
48
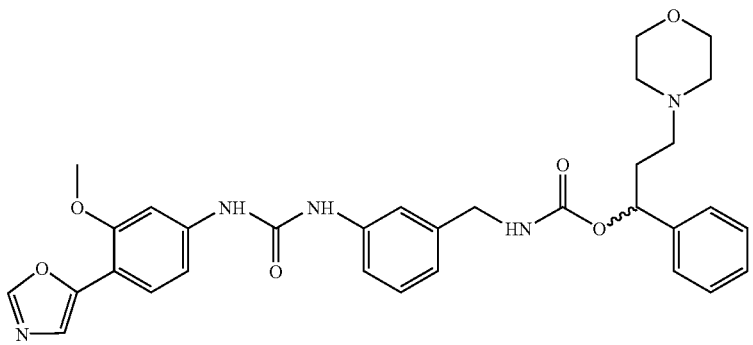
49
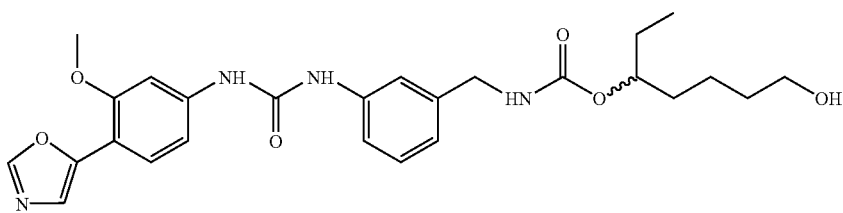
50
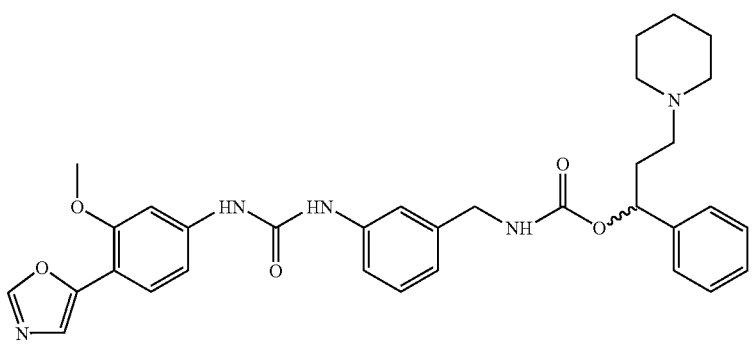
51
Chiral
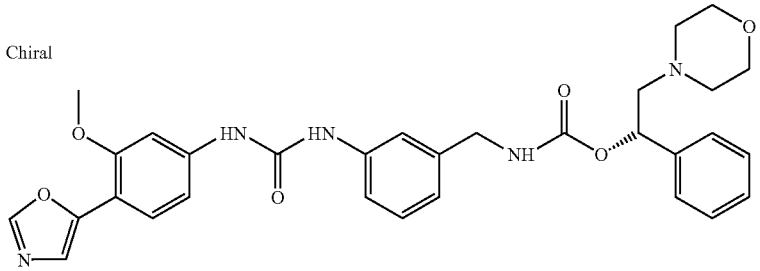
52
Chiral
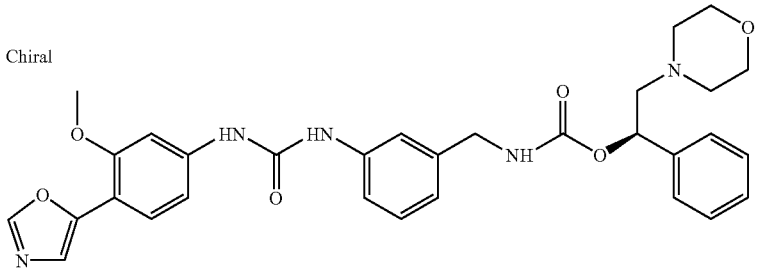

TABLE 1-continued
Compounds.
53
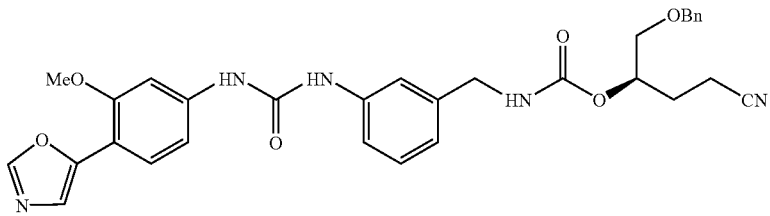
54
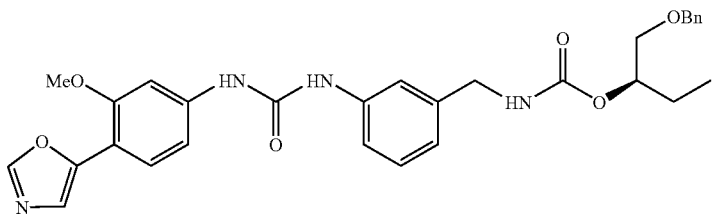
55
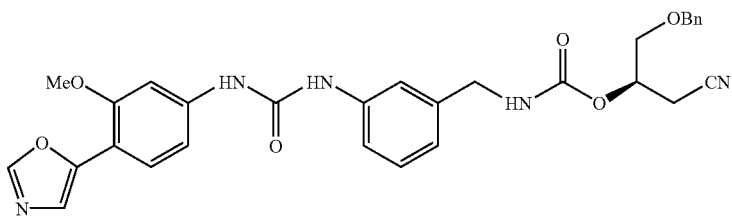
56
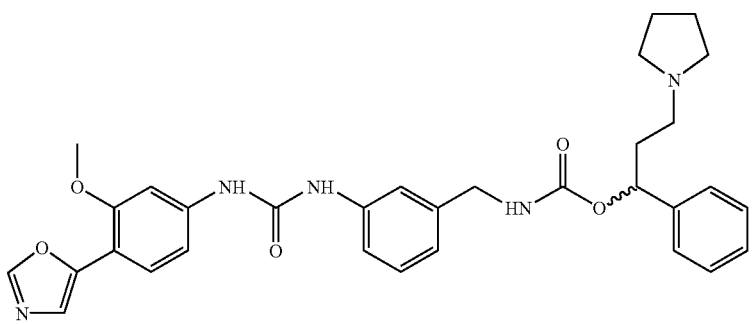
57
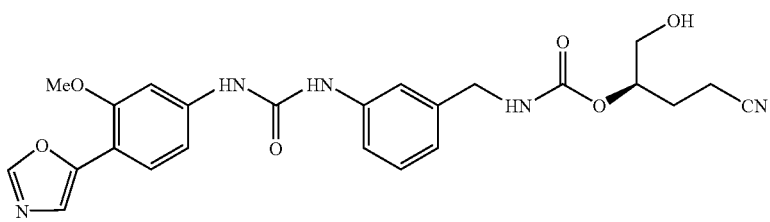
58
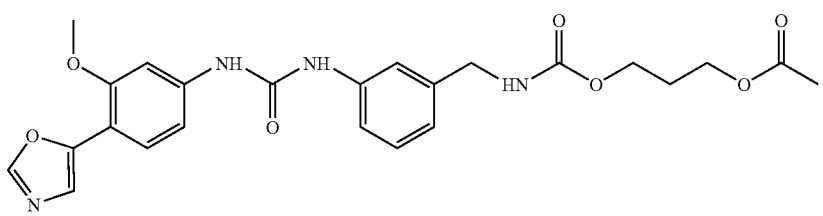

TABLE 1-continued

Compounds.

59

60

61 Chiral

62 Chiral

63

64

TABLE 1-continued
Compounds.
65
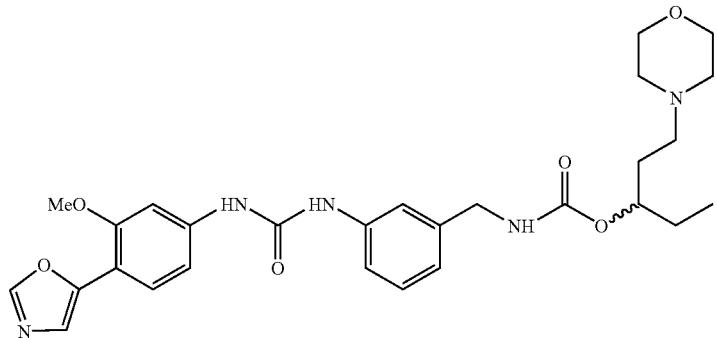
66 Chiral
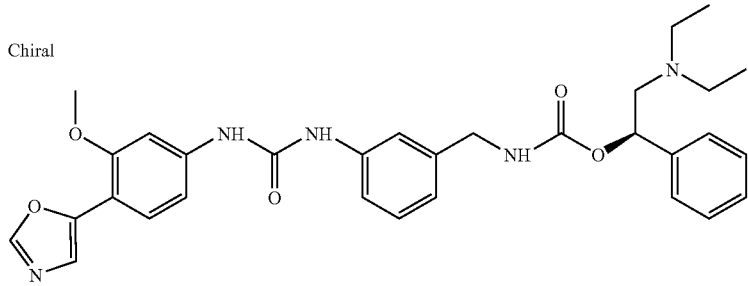
67 Chiral
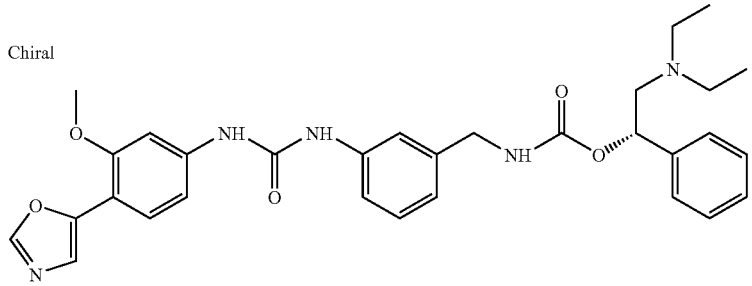
68 Chiral
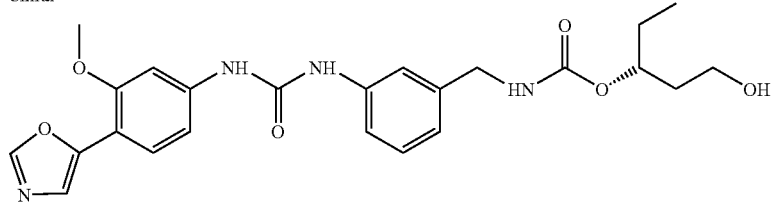
69 Chiral
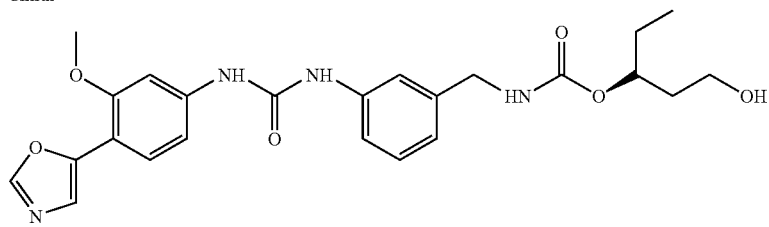

TABLE 1-continued

Compounds.

70

71

72

73

74

75

TABLE 1-continued

Compounds.

| 76 | (structure) |

| 77 Chiral | (structure) |

| 78 Chiral | (structure) |

| 79 | (structure) |

| 80 | (structure) |

TABLE 1-continued
Compounds.
81
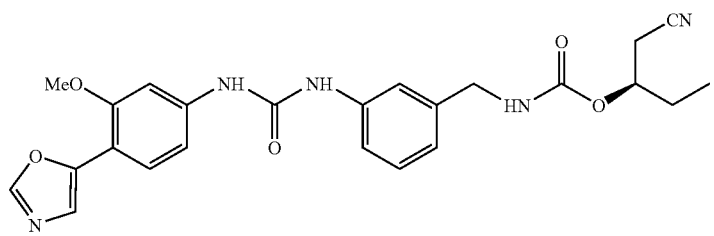
82
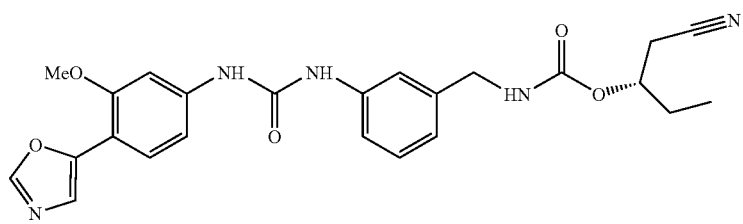
83
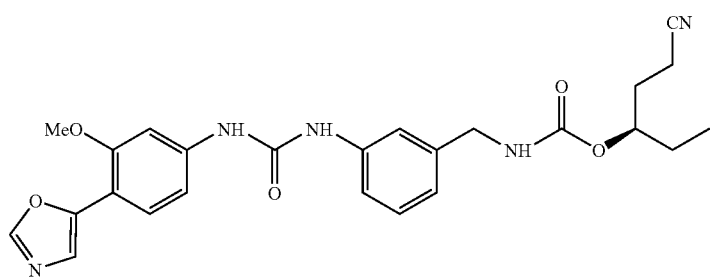
84
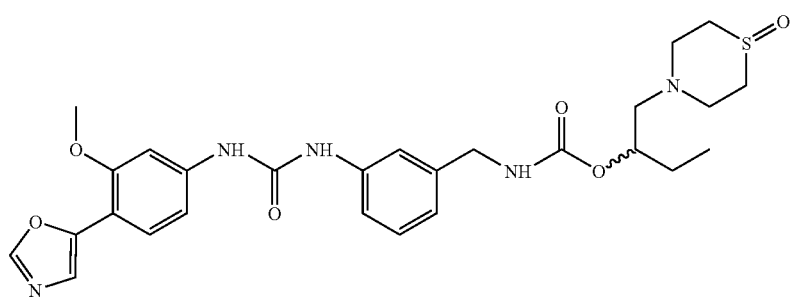
85
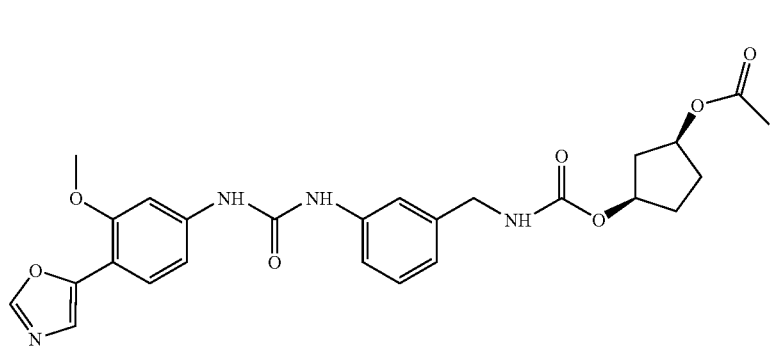

TABLE 1-continued
Compounds.
86
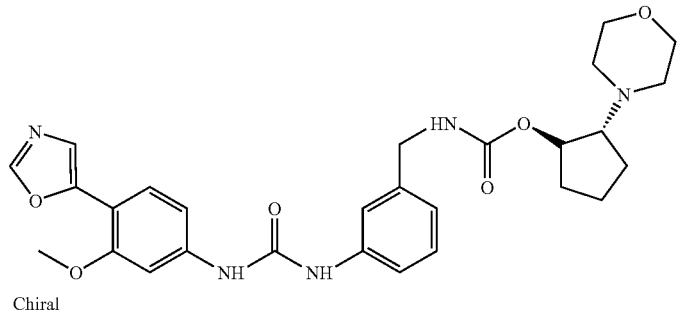
Chiral
87
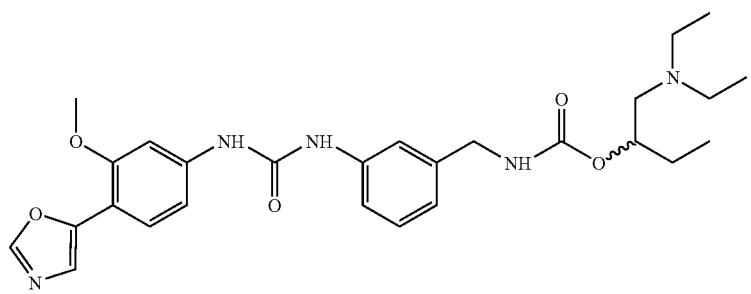
88
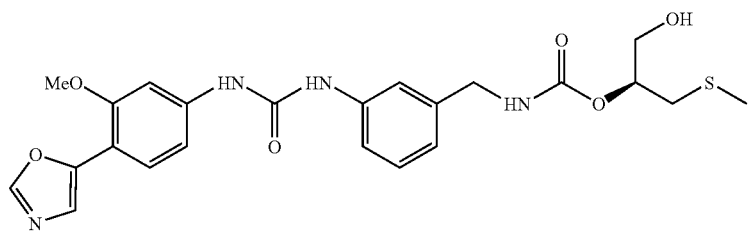
90
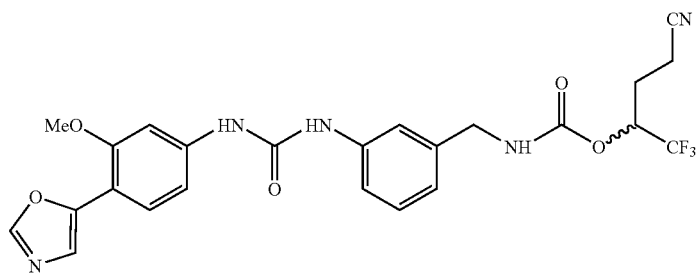
91
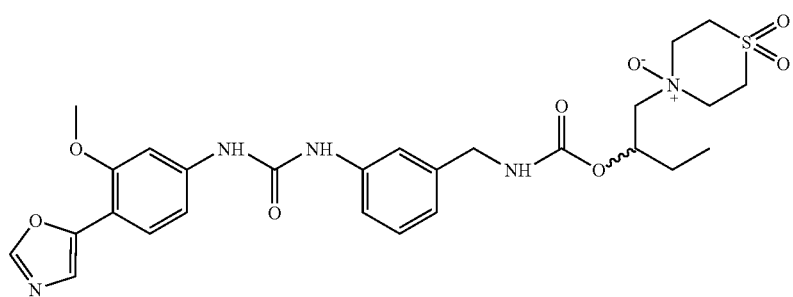

TABLE 1-continued
Compounds.
92
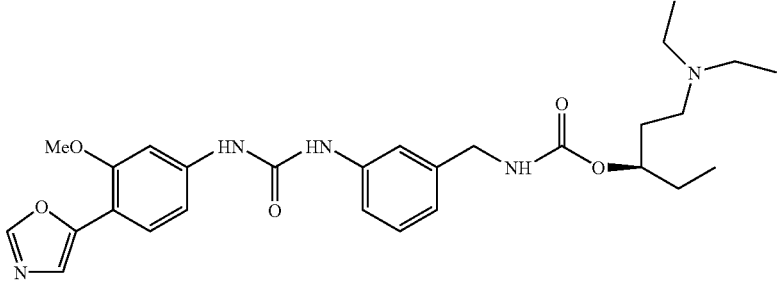
93
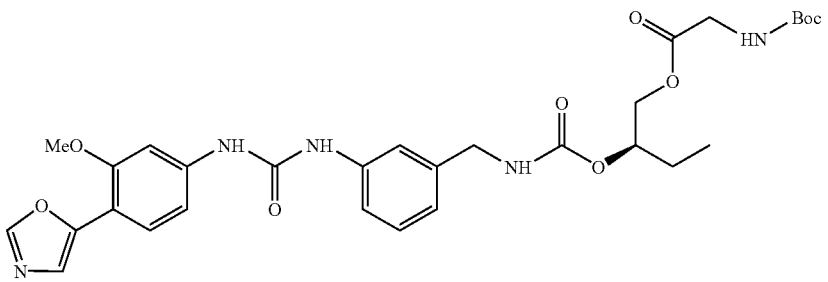
94
Chiral
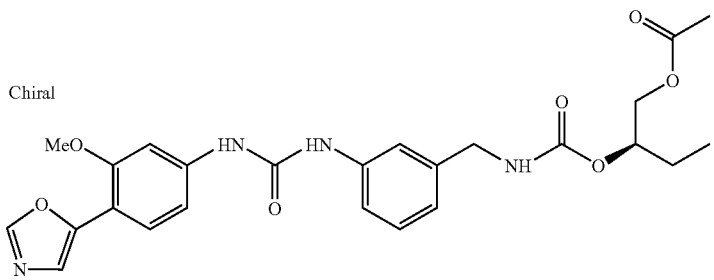
95
Chiral
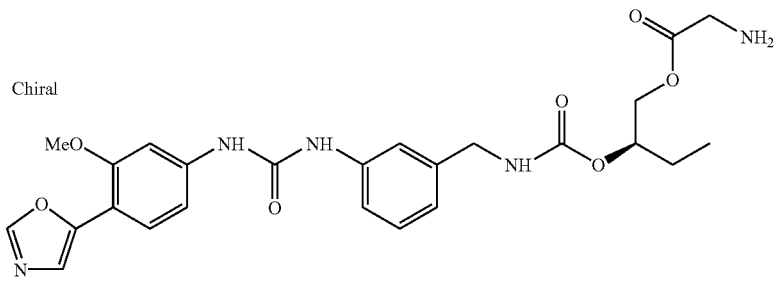
96
Chiral
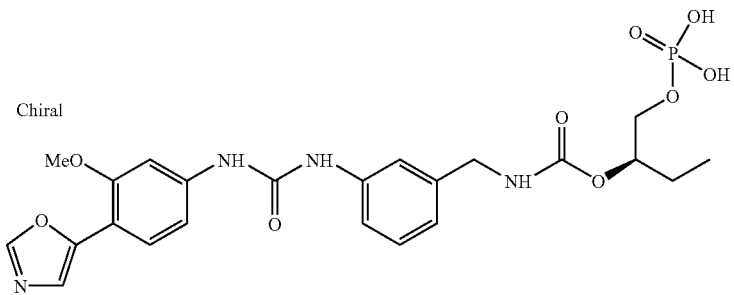

TABLE 1-continued
Compounds.
97
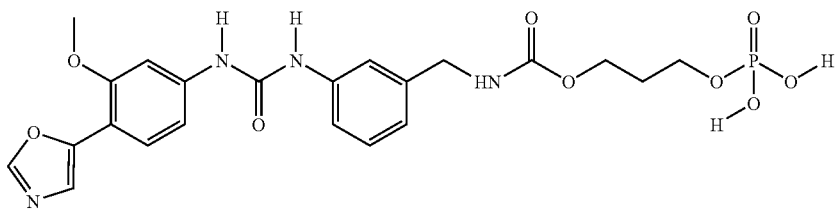
98
Chiral
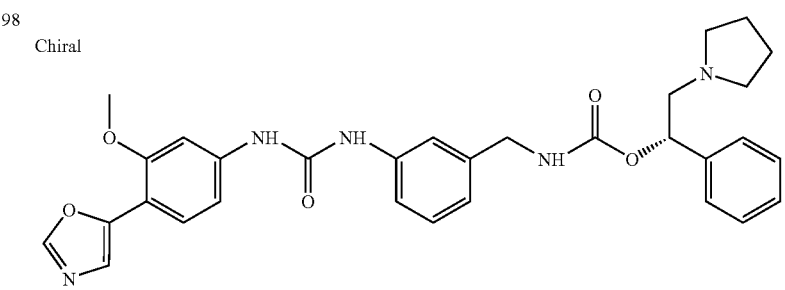
99
Chiral
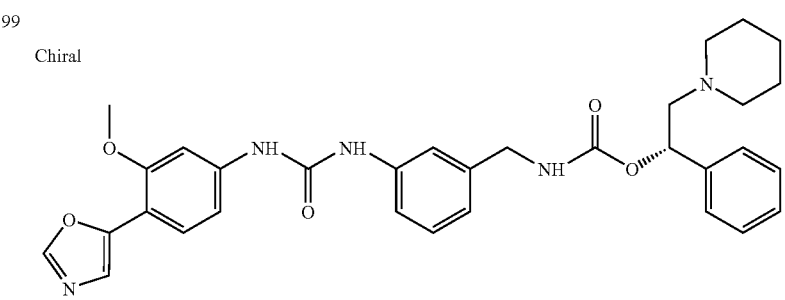
100
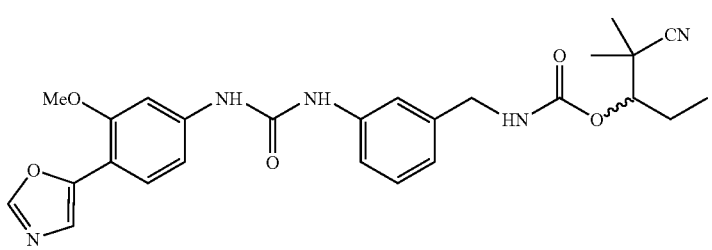
101
Chiral
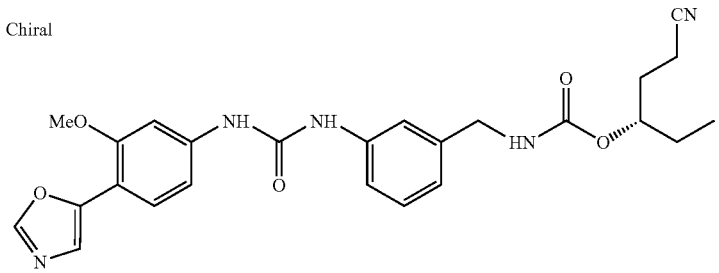

TABLE 1-continued
Compounds.
| 102 | 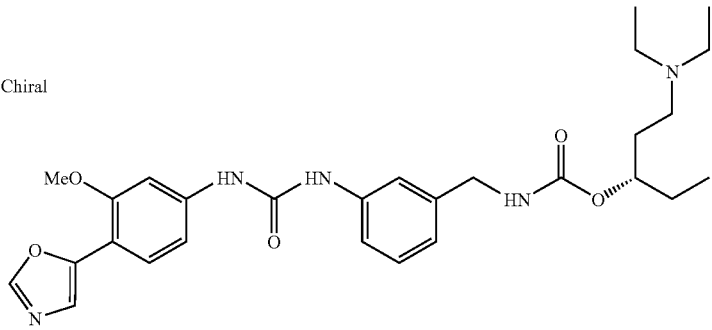 |
| --- | --- |
| 103 | 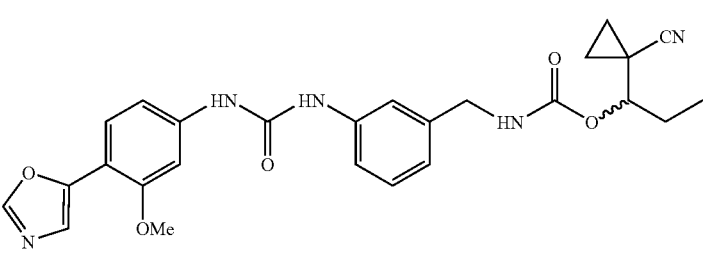 |
| 104 | 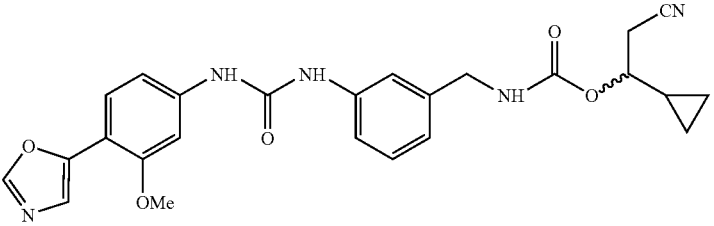 |
| 105 | 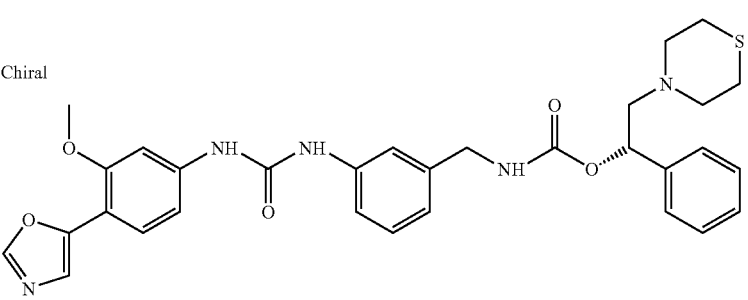 |
| 106 | 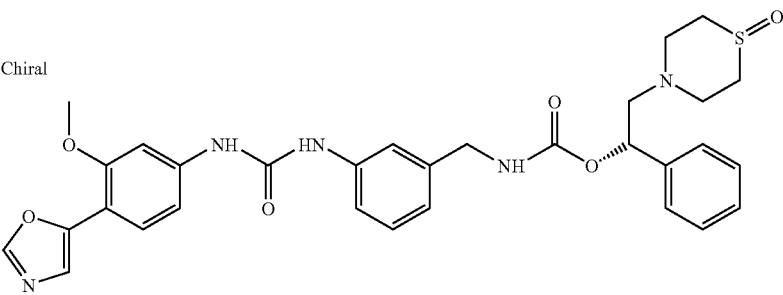 |

TABLE 1-continued
Compounds.
107
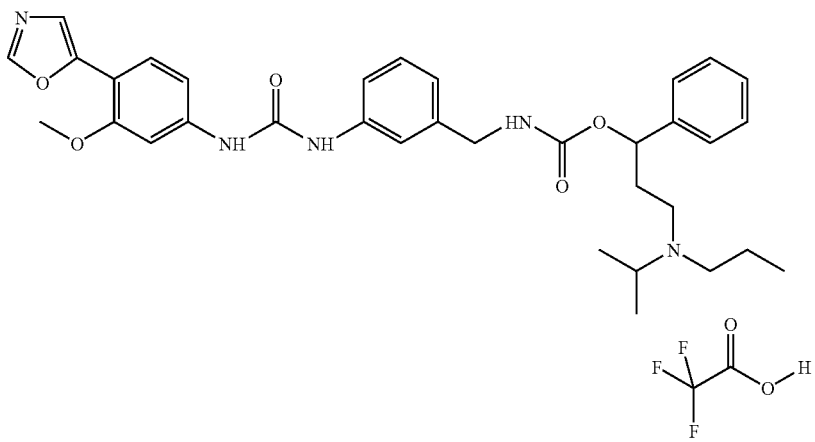
108
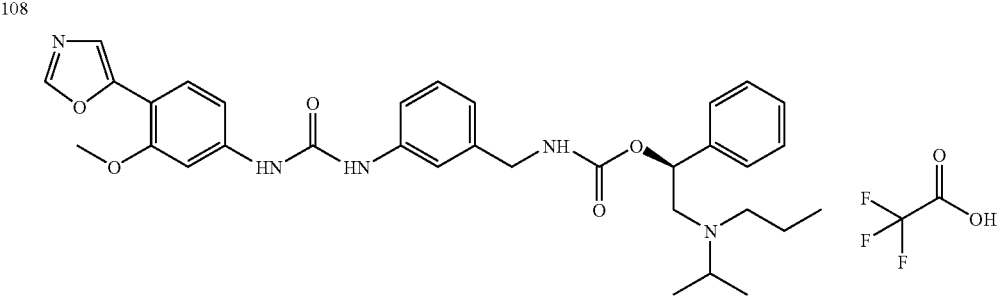
109
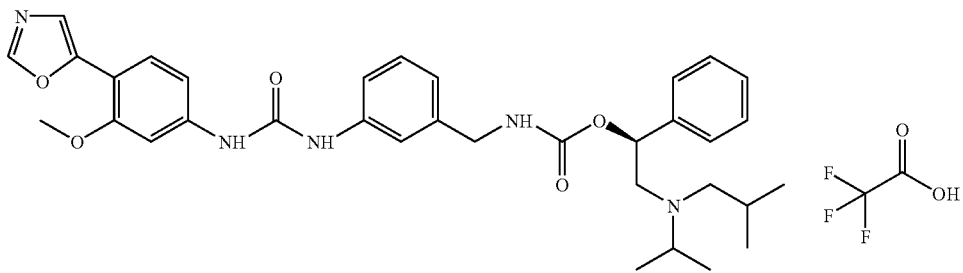
110
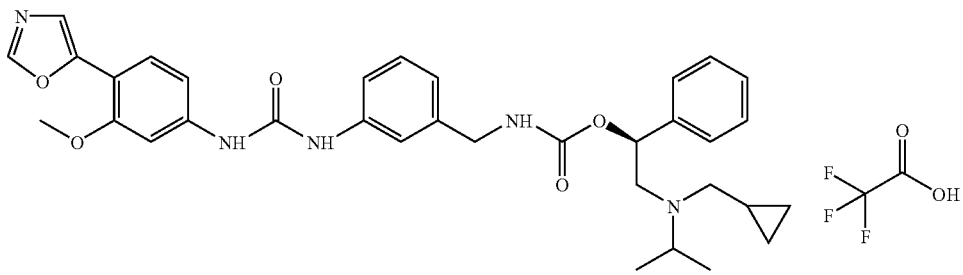

TABLE 1-continued
Compounds.
111
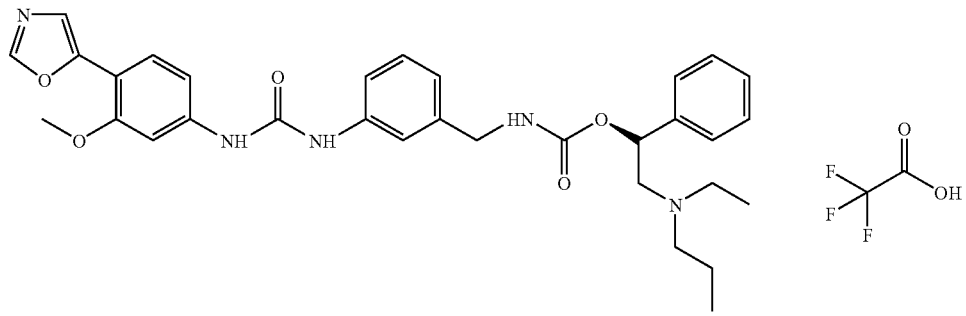
112
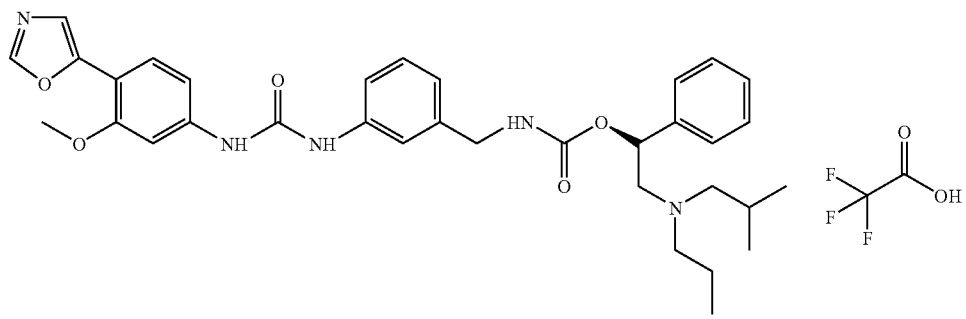
113
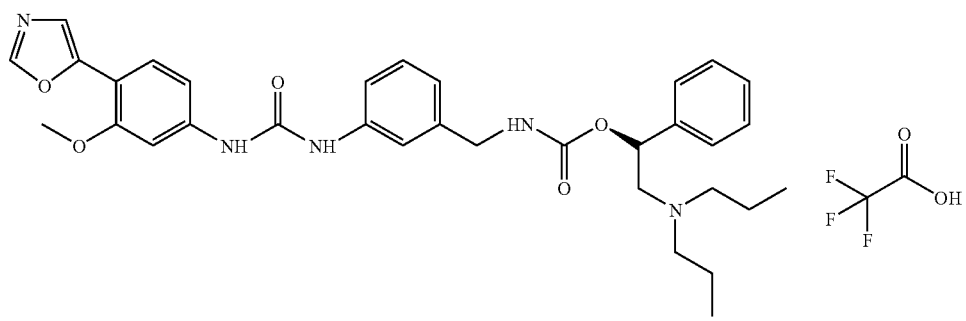
114
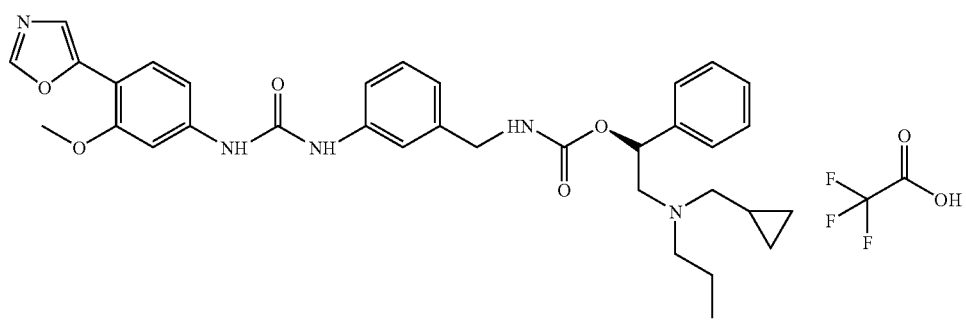

TABLE 1-continued

Compounds.

115

116

117

118

TABLE 1-continued

Compounds.

119

120

121

122

TABLE 1-continued
Compounds.
123
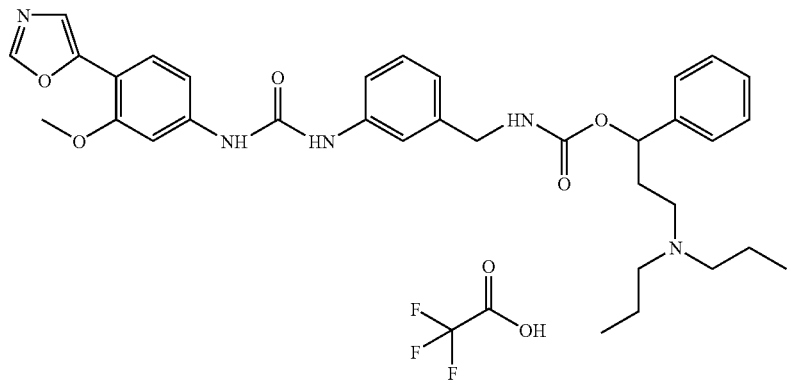
124
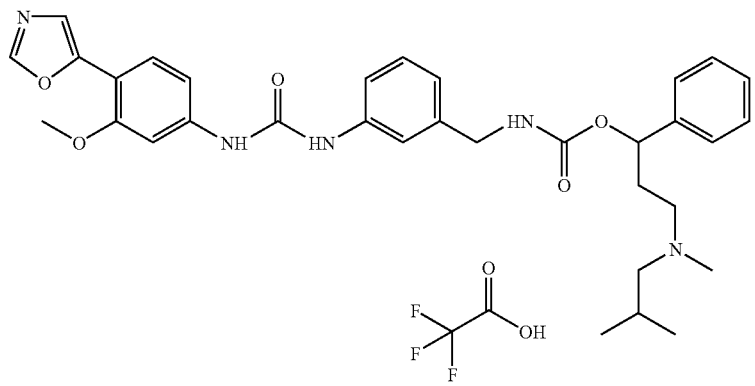
125
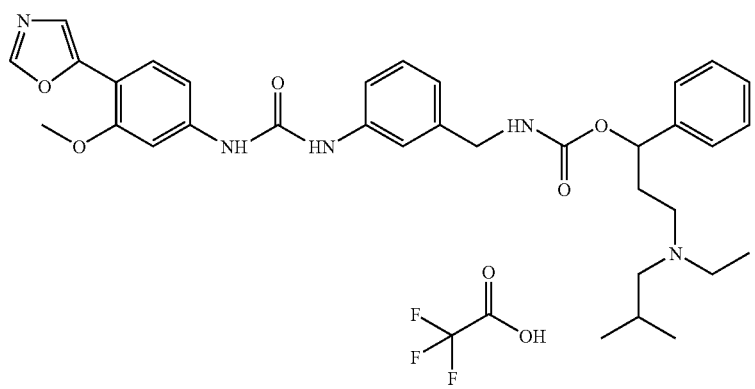
126
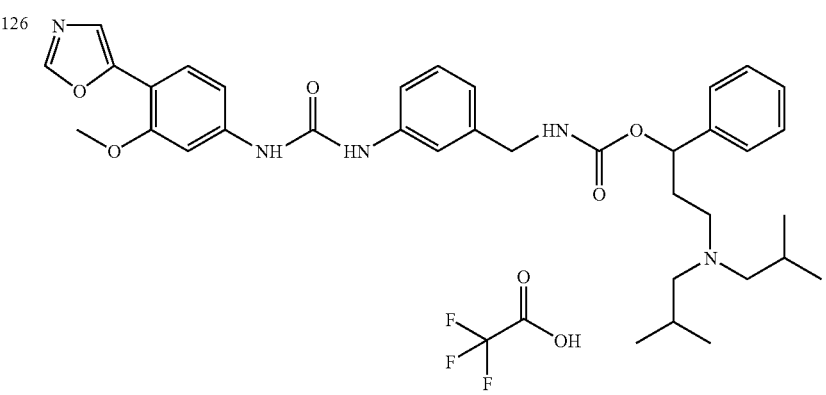

TABLE 1-continued
Compounds.
127 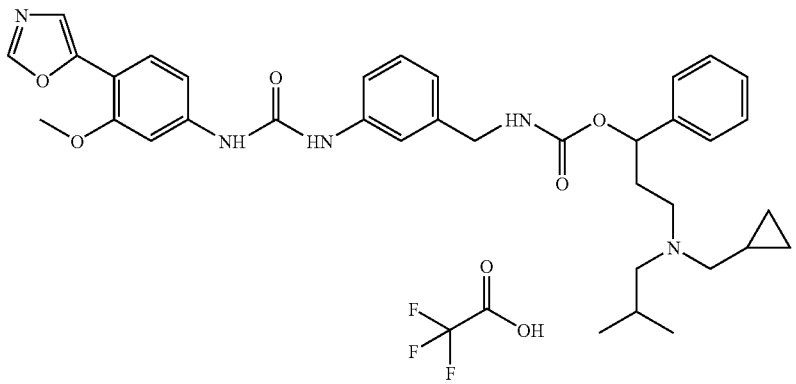
128 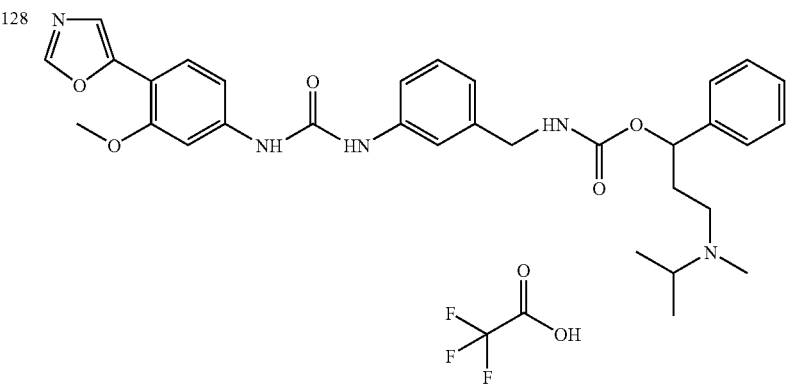
129 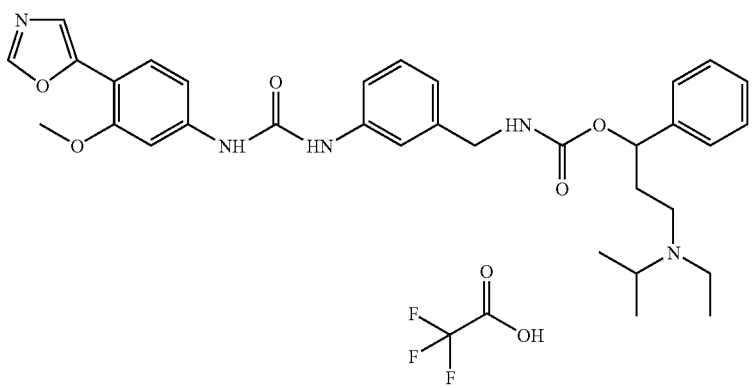
130 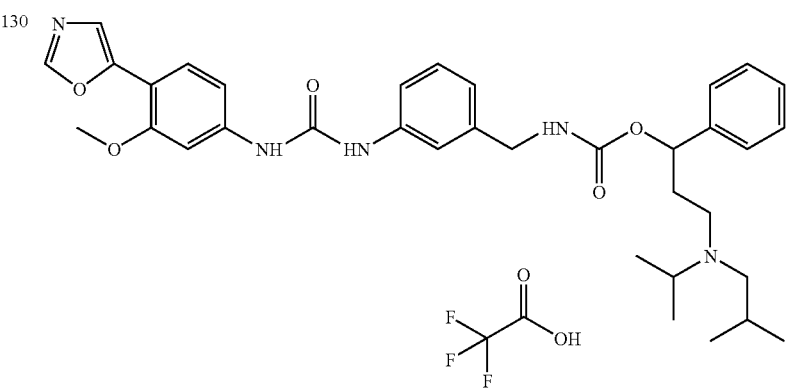

TABLE 1-continued
Compounds.
131 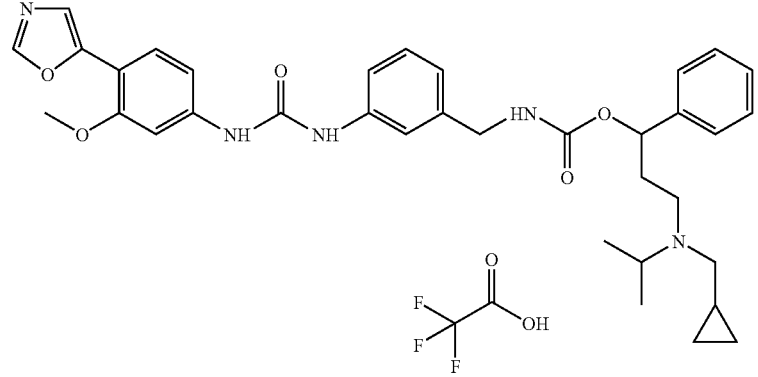
132 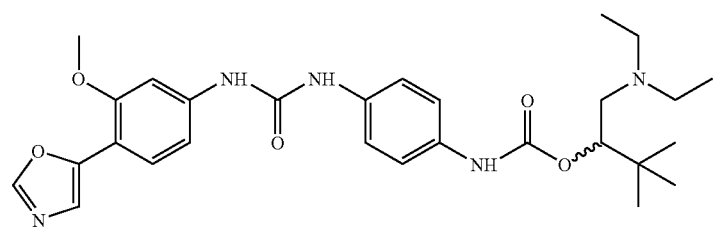
133 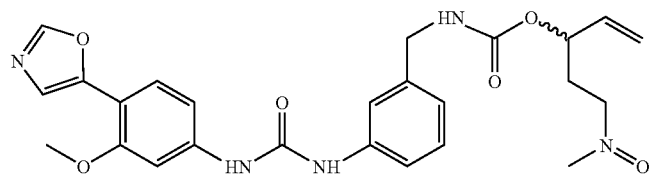
134 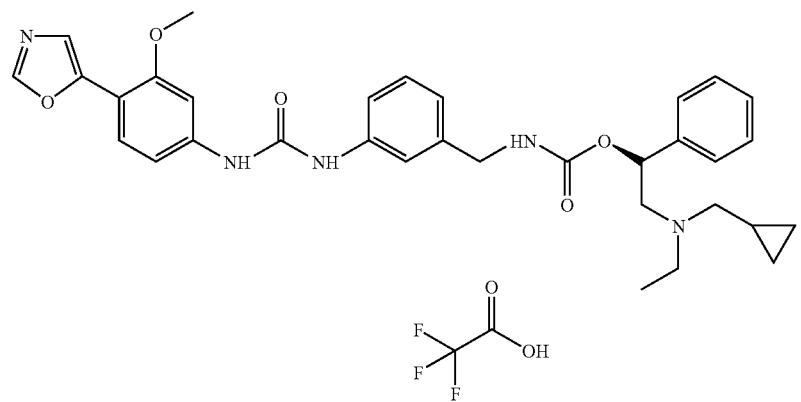
135 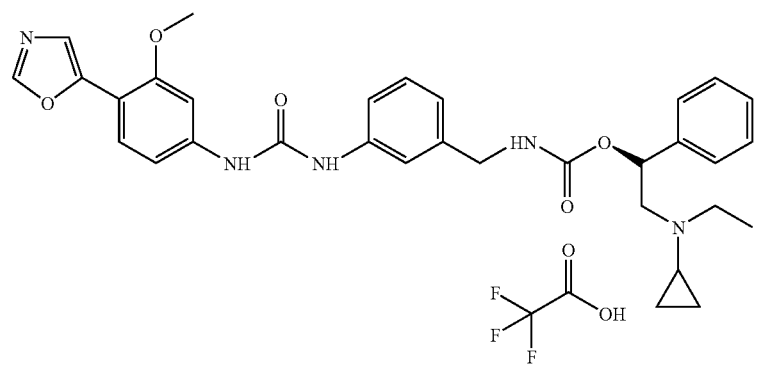

TABLE 1-continued
Compounds.
136
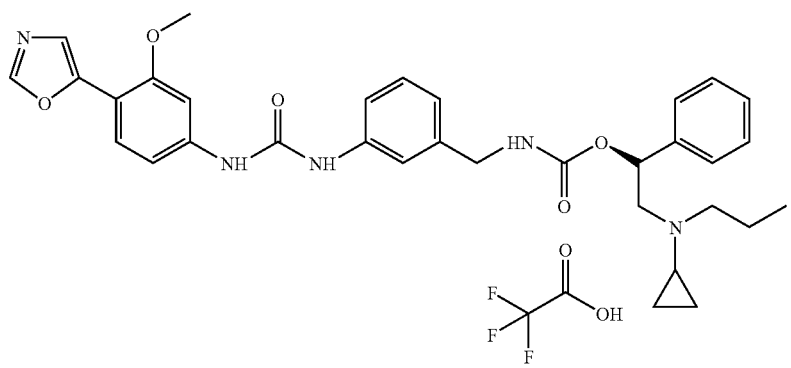
137
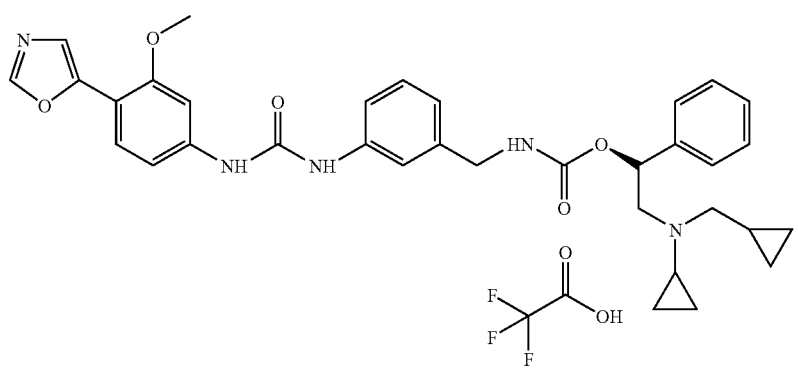
138
Chiral
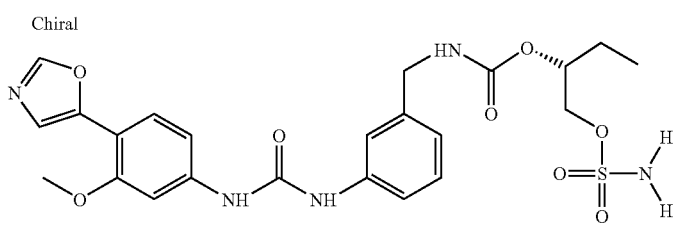
139
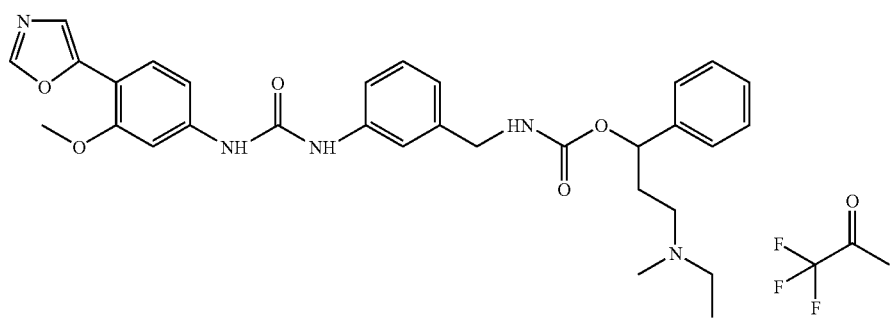

TABLE 1-continued
Compounds.
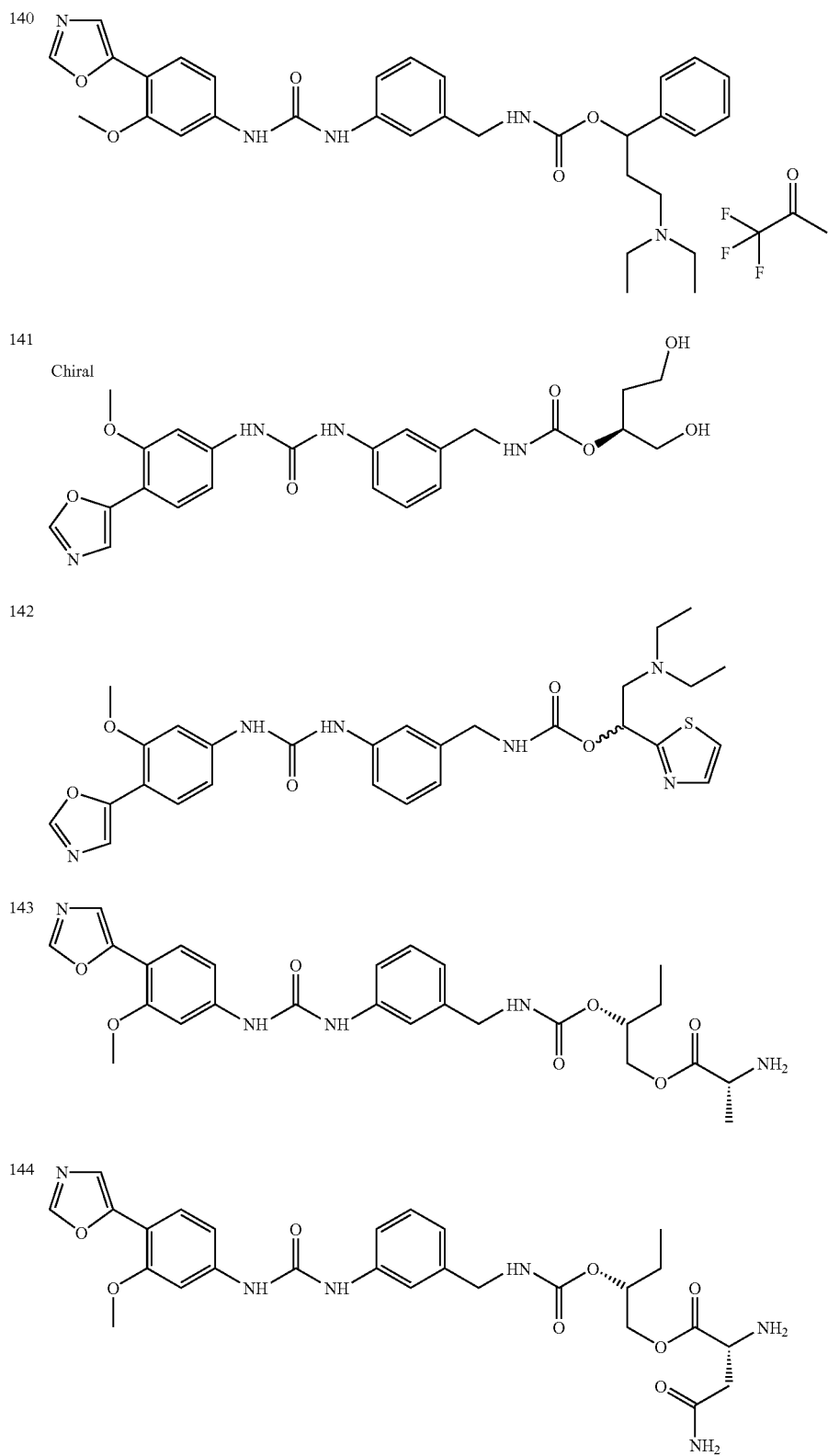

TABLE 1-continued
Compounds.
145
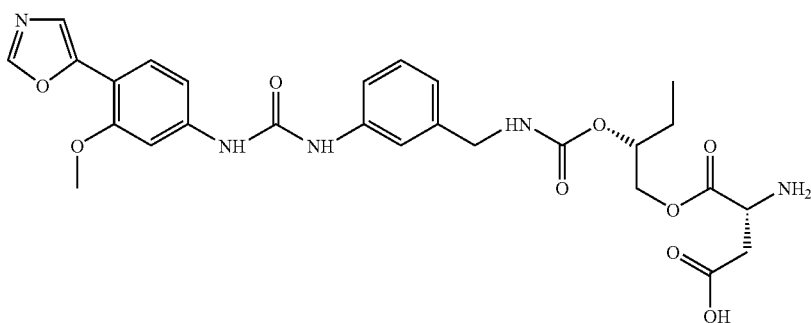
146
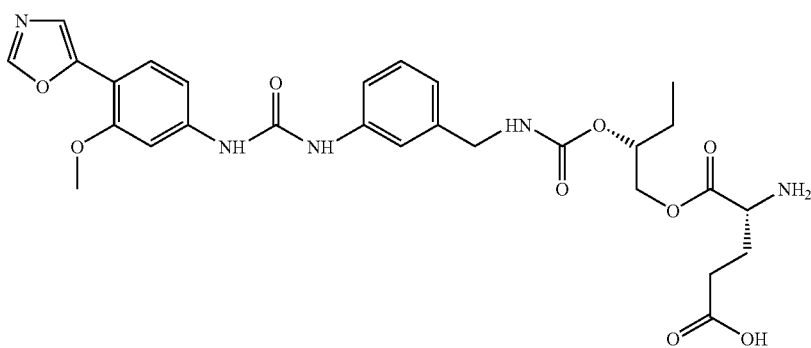
147
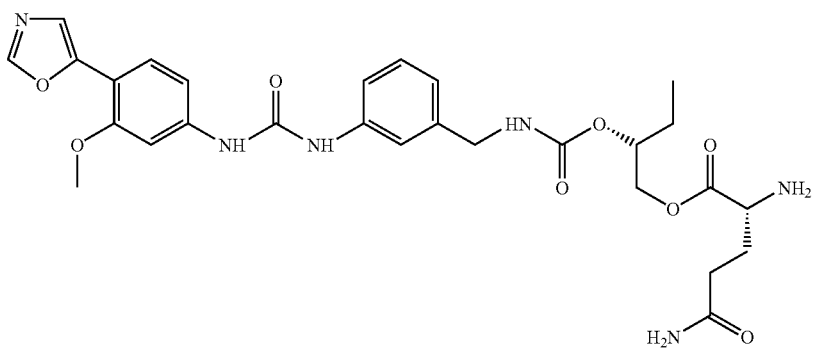
148
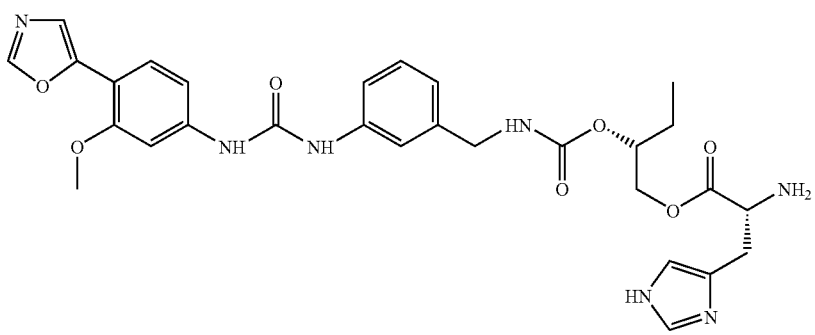

TABLE 1-continued
Compounds.
149
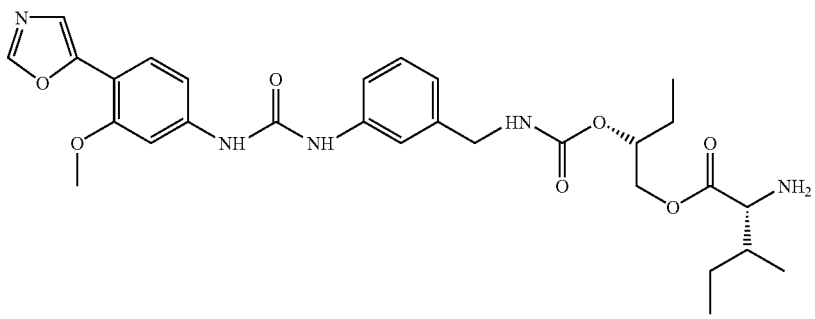
150
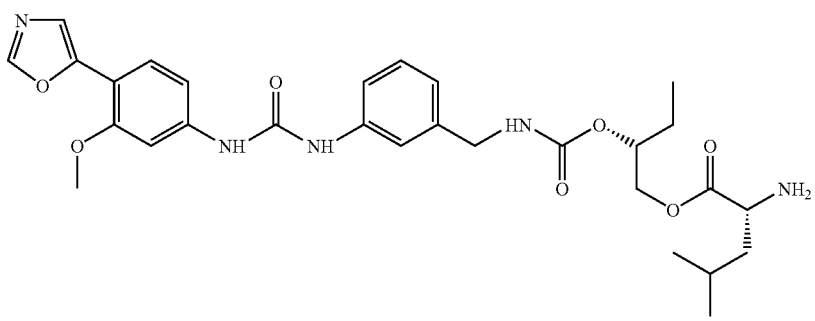
151
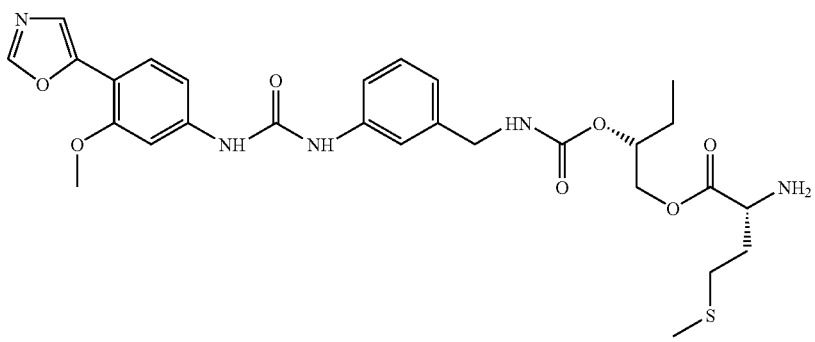
152
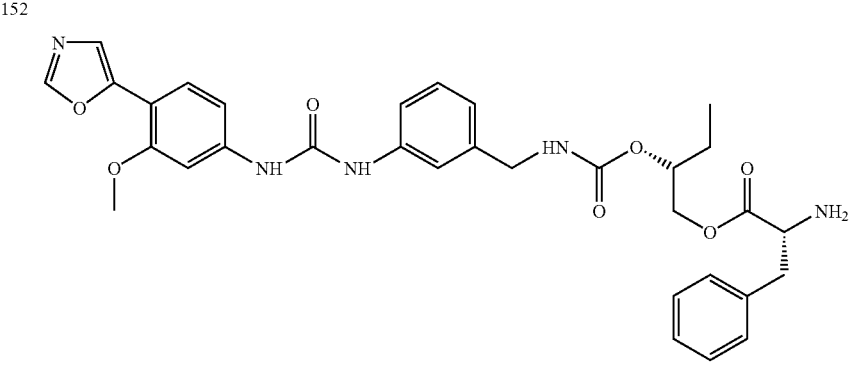

TABLE 1-continued
Compounds.
153 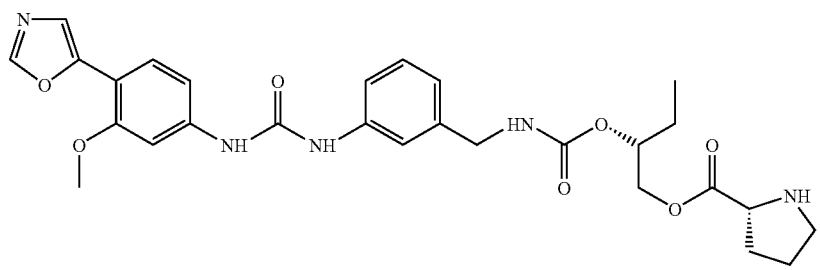
154 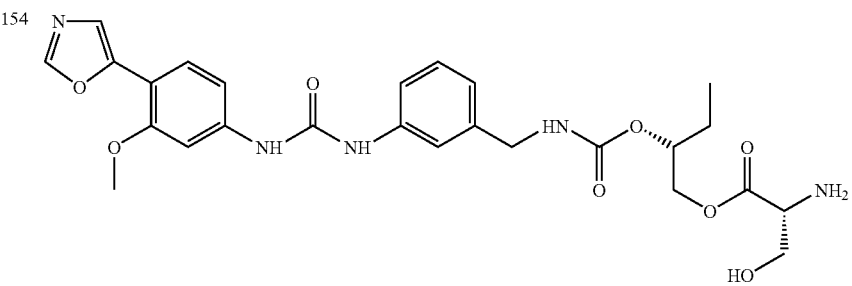
155 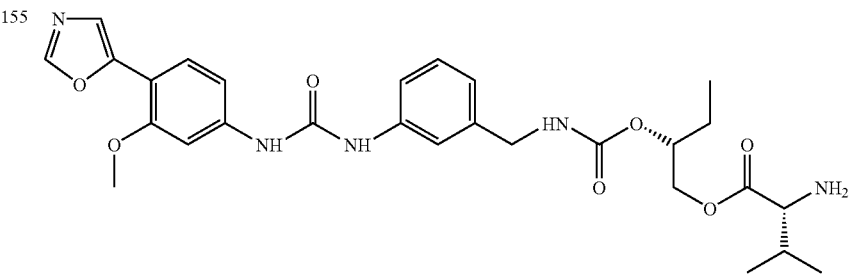
156 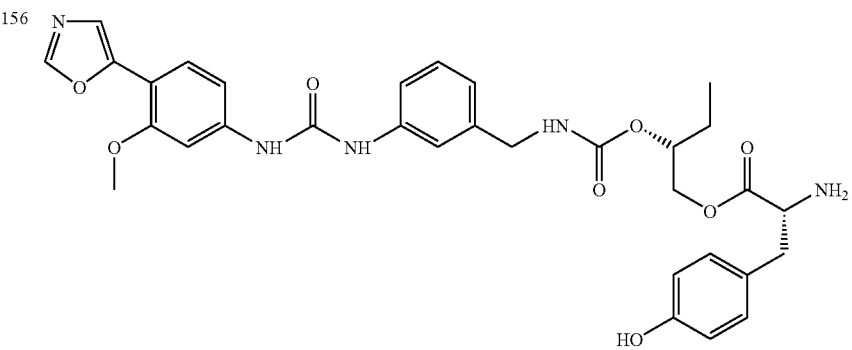
157 Chiral 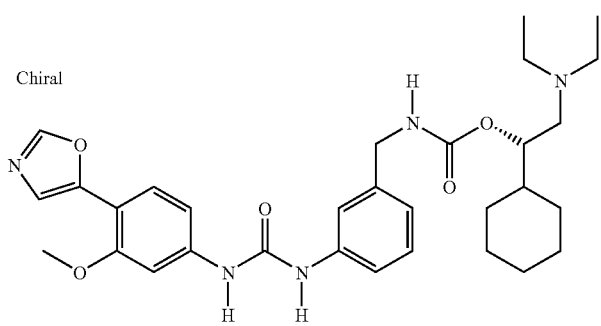

TABLE 1-continued

Compounds.

158
159
160
161
162

TABLE 1-continued

Compounds.

| 163 | (structure) |
| 164 | (structure) |
| 165 | (structure) |
| 166 Chiral | (structure) |
| 167 Chiral | (structure) |
| 168 Chiral | (structure) |
| 169 Chiral | (structure) |

TABLE 1-continued

Compounds.

| 170 | Chiral (structure) |
| 171 | Chiral (structure) |
| 172 | Chiral (structure) |
| 173 | Chiral (structure) |
| 174 | Chiral (structure) |
| 175 | Chiral (structure) |
| 176 | Chiral (structure) |

TABLE 1-continued
Compounds.
177 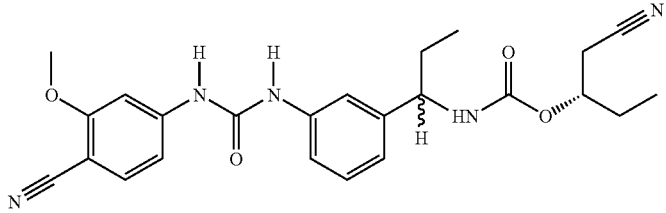
178 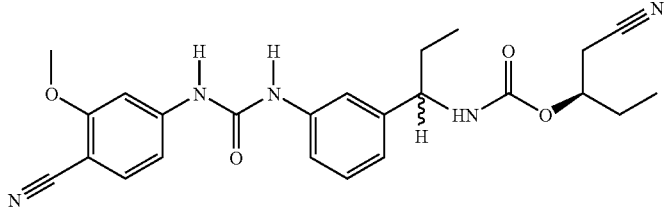
179 Chiral 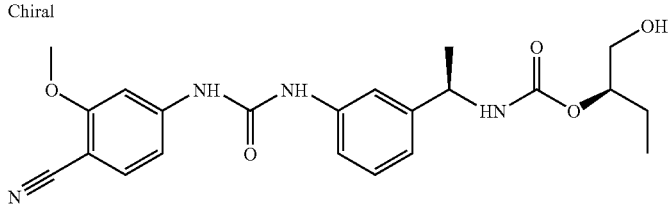
180 Chiral 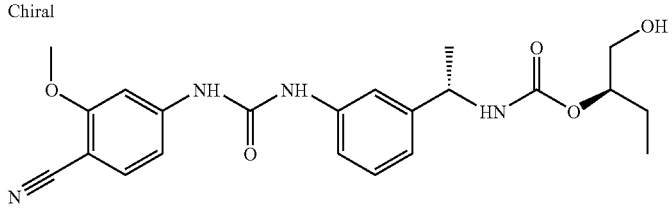
181 Chiral 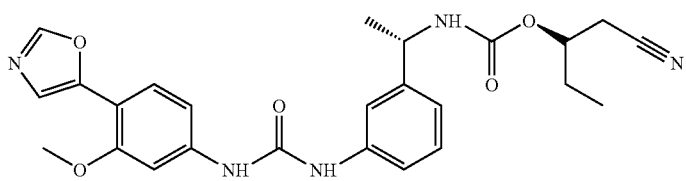
182 Chiral 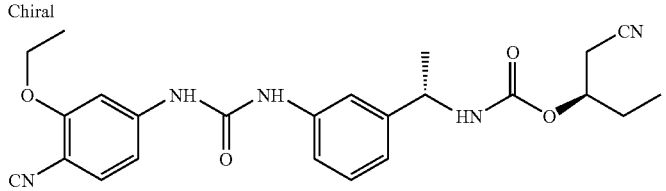
183 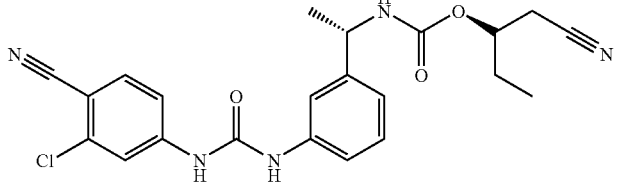

TABLE 1-continued

Compounds.

184 Chiral

[Chemical structure: 4-cyano-3-methoxyphenyl urea linked to 3-[(1S)-1-(((S)-tetrahydrofuran-3-yloxy)carbonylamino)ethyl]phenyl]

185 Chiral

[Chemical structure: 4-cyano-3-methoxyphenyl urea linked to 3-[(1S)-1-(((R)-tetrahydrofuran-3-yloxy)carbonylamino)ethyl]phenyl]

186 Chiral

[Chemical structure: 3-ethoxy-4-cyanophenyl urea linked to 3-[(1S)-1-(((S)-tetrahydrofuran-3-yloxy)carbonylamino)ethyl]phenyl]

187

[Chemical structure: 3-chloro-4-cyanophenyl urea linked to 3-[1-(((S)-tetrahydrofuran-3-yloxy)carbonylamino)ethyl]phenyl]

In the above table, certain compounds are shown as salts. It should be understood that the scope of the compounds set forth in any given entry in the table covers all forms of the depicted compound, not just the salt shown.

When stereochemistry is not specifically indicated, the compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention, unless otherwise indicated. Each stereogenic carbon may be of the R or S configuration.

Combinations of substituents and variables envisioned by this invention are only those that result in the formation of stable compounds. The term "stable", as used herein, refers to compounds that possess stability sufficient to allow manufacture and maintenance of the integrity for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

As used herein, the compounds of this invention, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those which increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of the compounds of this invention.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of this invention may be synthesized using conventional techniques. Advantageously, these compounds are conveniently synthesized from readily available starting materials. More specifically, the compounds of this invention may be synthesized by the schemes set forth in Examples 1 and 2 with modifications that will be readily apparent to those of skill in the art.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The novel compounds of the present invention are excellent ligands for IMPDH. Accordingly, these compounds are capable of targeting and inhibiting IMPDH enzyme. Inhibition can be measured by various methods, including, for example, IMP dehydrogenase HPLC assays (measuring enzymatic production of XMP and NADH from IMP nd NAD) and IMP dehydrogenase spectrophotometric assays (measuring enzymatic production of NADH from NAD). [See C. Montero et al., *Clinica Chimica Acta*, 238, pp. 169–178 (1995)].

Compositions of this invention comprise a compound of this invention or a salt thereof; an additional agent selected from an immunosuppressant, an anti-cancer agent, an antiviral agent, anti-inflammatory agent, antifungal agent, antibiotic, or an anti-vascular hyperproliferation compound; and any pharmaceutically acceptable carrier, adjuvant or vehicle. Alternate compositions of this invention comprise a compound of this invention or a salt thereof; and a pharmaceutically acceptable carrier, adjuvant or vehicle. Such composition may optionally comprise an additional agent selected from an immunosuppressant, an anti-cancer agent, an antiviral agent, anti-inflammatory agent, antifungal agent, antibiotic, or an anti-vascular hyperproliferation compound. Preferably, the compositions of this invention are pharmaceutical compositions.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d$\alpha$-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-$\beta$-cyclodextrins, or other solubilized derivatives may also be advantageously used to enhance delivery of compounds of this invention.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica, *Ph. Helv.*, or a similar alcohol, or carboxymethyl cellulose or similar dispersing agents which are commonly used in the formulation of pharmaceutically acceptable dosage forms such as emulsions and or suspensions Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions and/or emulsions are administered orally, the active ingredient may be suspended or dissolved in an oily phase and combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the IMPDH inhibitory compounds described herein are useful in a monotherapy and/or in combination therapy for the prevention and treatment of IMPDH-mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of an IMPDH inhibitor of this invention and one or more additional therapeutic or prophylactic agents, both the IMPDH inhibitor and the additional agent should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, interferon and mizoribine.

According to an alternate embodiment, the pharmaceutical compositions of this invention may additionally comprise an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines, interferon and thioxantheres.

According to another alternate embodiment, the pharmaceutical compositions of this invention may additionally comprise an anti-viral agent. Examples of anti-viral agents include, but are not limited to, Cytovene, Ganciclovir, trisodium phosphonoformate, Ribavirin, d4T, ddI, AZT, and acyclovir.

According to yet another alternate embodiment, the pharmaceutical compositions of this invention may additionally comprise an anti-vascular hyperproliferative agent. Examples of anti-vascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, the patient's disposition to the disease and the judgment of the treating physician.

In an alternate embodiment, this invention provides methods of treating or preventing IMPDH-mediated disease in a mammal comprising the step of administrating to said mammal any of the pharmaceutical compositions and combinations described above. If the pharmaceutical composition only comprises the IMPDH inhibitor of this invention as the active component, such methods may additionally comprise the step of administering to said mammal an agent selected from an anti-inflammatory agent, immunosuppressant, an anti-cancer agent, an anti-viral agent, or an anti-vascular hyperproliferation compound. Such additional agent may be administered to the mammal prior to, concurrently with, or following the administration of the IMPDH inhibitor composition.

In a preferred embodiment, these methods are useful in suppressing an immune response in a mammal. Such methods are useful in treating or preventing diseases, including, transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhea, pulmonary inflammation, eye uveitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis.

These methods comprise the step of administering to the mammal a composition comprising a compound of this invention and a pharmaceutically acceptable adjuvant. In a preferred embodiment, this particular method comprises the additional step of administering to said mammal a composition comprising an additional immunosuppressant and a pharmaceutically acceptable adjuvant.

Alternatively, this method comprises the step of administering to said mammal a composition comprising a compound of this invention; an additional immunosuppressive agent and a pharmaceutically acceptable adjuvant.

In an alternate preferred embodiment, these methods are useful for inhibiting viral replication in a mammal. Such methods are useful in treating or preventing DNA and RNA viral diseases caused by infection for example, by orthomyxoviruses (influenza viruses types A and B), paramyxoviruses (respiratory syncytial virus (RSV), subacute sclerosing panencephalitis (SSPE) virus) measles and parainfluenza type 3), herpesviruses (HSV-1, HSV-2, HHV-6, HHV-7, HHV-8, Epstein Barr Virus (EBV), cytomegalovirus (HCMV) and varicella zoster virus (VZV)), retroviruses (HIV-1, HIV-2, HTLV-1, HTLV-2), flavi- and pestiviruses (yellow fever virus (YFV), hepatitis C virus (HCV), dengue fever virus, bovine viral diarrhea virus (BVDV), hepatotrophic viruses (hepatitis A virus (HAV), hepatitis B virus (HBV), hepatitis D virus (HDV), hepatitis E virus (HEV), hepatitis G virus (HGV), Crimean-Congo hemorrhagic fever virus (CCHF), bunyaviruses (Punta Toro virus, Rift Valley fever virus (RVFV), and sandfly fever Sicilian virus), Hantaan virus, Caraparu virus), human papilloma viruses, encephalitis viruses (La Crosse virus), arena viruses (Junin and Tacaribe virus), reovirus, vesicular stomatitis virus, rhinoviruses, enteroviruses (polio virus, coxsackie viruses, encephalomyocarditis virus (EMC)), Lassa fever virus, and togaviruses (Sindbis and Semlike forest viruses) and poxyiruses (vaccinia virus), adenoviruses, rubiola, and rubella.

These methods comprise the step of administering to the mammal a composition comprising a compound of this invention, and a pharmaceutically acceptable adjuvant. In a preferred embodiment, this particular method comprises the additional step of administering to said mammal a composition comprising an additional anti-viral agent and a pharmaceutically acceptable adjuvant.

Alternatively, this method comprises the step of administering to said mammal a composition comprising a compound of this invention; an additional anti-viral agent and a pharmaceutically acceptable adjuvant.

In another alternate preferred embodiment, these methods are useful for inhibiting vascular cellular hyperproliferation in a mammal. Such methods are useful in treating or preventing diseases, including, restenosis, stenosis, artherosclerosis and other hyperproliferative vascular disease.

These methods comprise the step of administering to the mammal a composition comprising a compound of this invention, and a pharmaceutically acceptable adjuvant. In a preferred embodiment, this particular method comprises the additional step of administering to said mammal a composition comprising an additional anti-vascular hyperproliferative agent and a pharmaceutically acceptable adjuvant.

Alternatively, this method comprises the step of administering to said mammal a composition comprising a compound of this invention; an additional anti-vascular hyperproliferative agent and a pharmaceutically acceptable adjuvant.

In another alternate preferred embodiment, these methods are useful for inhibiting tumors and cancer in a mammal. Such methods are useful in treating or preventing diseases, including, tumors and malignancies, such as lymphoma, leukemia and other forms of cancer.

These methods comprise the step of administering to the mammal a composition comprising a compound of this invention, and a pharmaceutically acceptable adjuvant. In a preferred embodiment, this particular method comprises the additional step of administering to said mammal a composition comprising an additional anti-tumor or anti-cancer agent and a pharmaceutically acceptable adjuvant.

Alternatively, this method comprises the step of administering to said mammal a composition comprising a compound of this invention; an additional anti-tumor or anti-cancer agent and a pharmaceutically acceptable adjuvant.

In another alternate preferred embodiment, these methods are useful for inhibiting inflammation and inflammatory diseases in a mammal. Such methods are useful in treating or preventing diseases, including, osteoarthritis, acute pancreatitis, chronic pancreatitis, asthma and adult respiratory distress syndrome.

These methods comprise the step of administering to the mammal a composition comprising a compound of this invention, and a pharmaceutically acceptable adjuvant. In a preferred embodiment, this particular method comprises the additional step of administering to said mammal a composition comprising an anti-inflammatory agent and a pharmaceutically acceptable adjuvant.

In order that this invention be more fully understood, the following examples are set forth. These examples are for the purpose of illustration only and are not to be construed as limiting the scope of the invention in any way.

EXAMPLE 1

Synthesis of Compound 41

A. Synthesis of C4

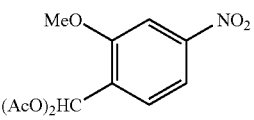
C1

To a solution of glacial acetic acid (46 mL), acetic anhydride (46 mL, 485 mmole) and 2-methyl-5-nitroanisole (10.0 g, 60 mmole) at 0° C. was added conc. H$_2$SO$_4$ (6.9 mL) in a dropwise fashion. Upon complete addition, CrO$_3$ (8.08 g, 80.8 mmole) was added portion-wise over 60 mins. Following an additional 15 mins of stirring at 0° C., the reaction mixture was poured over ice and the resulting precipitate was isolated by filtration, rinsing with cold H$_2$O. Purification by flash chromatography, eluting with a gradient of 15–50% EtOAc in hexanes, provided 8.14 g (24%, 51% based on recovered starting material) C1 as a white solid. The $^1$H NMR was consistent with that of the desired structure.

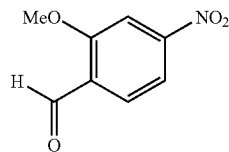
C2

A stirred suspension of C1 (81.94 g, 307 mmole) in dioxane (100 mL) was treated with concentrated HCl (20 mL) and heated at reflux overnight. Upon cooling to ambient temperature, the product C2 precipitated as a light yellow crystalline solid in a yield of 40.65 g (73.1%). The filtrate was concentrated to a volume of ca. 80 mL and a second crop of product crystals was driven from solution by the addition of hexanes, yielding 8.91 g (16.0%). Both batches were identical by $^1$H NMR and TLC analysis and were consistent with that of the desired material. The total yield of C2 was 49.56 g (89.1%).

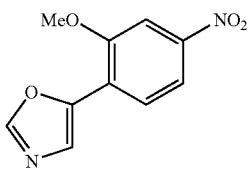
C3

A solution of C2 (456 mg, 2.51 mmole), tosylmethyl isocyanide (490 mg, 2.51 mmole) and K$_2$CO$_3$ (347 mg, 251 mmole) were dissolved in methanol and heated to reflux for 1.5 hours. The product mixture was then concentrated in vacuo, redissolved in CH$_2$Cl$_2$, washed with water and brine, dried over Na$_2$SO$_4$ and again concentrated in vacuo. Purified product C3 was obtained through recrystallization (Et$_2$O/hexanes) to yield 375 mg (68%). The $^1$H NMR was consistent with that of the desired structure.

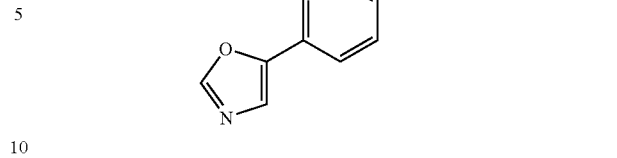
C4

A solution of C3 (4.214 g, 19.1 mmole) in EtOAc (150 mL) was treated with 10% Pd/C (1.05 g, 25 wt. % of C3) and subjected to 40 psi H$_2$(g) (Parr Hydrogenation Apparatus) overnight. The reaction mixture was filtered and concentrated in vacuo. Pure product C4 was obtained through flash chromatography, eluting with a gradient of 30–40% EtOAc/hexanes, in a yield of 3.4 g (93%). The $^1$H NMR was consistent with that of the desired structure.

B. Synthesis of Compound I113

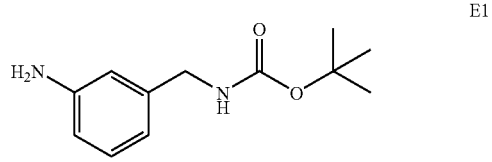
E1

A solution of 3-aminobenzylamine (826 mg, 6.87 mmole) and triethylamine (2.39 mL, 17.18 mmole) was treated with di-t-butyldicarbonate (1.50 g, 6.87 mmole) and the mixture was stirred at ambient temperature for 2 hours. The reaction was then diluted with CH$_2$Cl$_2$, washed with NaHCO$_3$(aq), water and brine, dried (Na$_2$SO$_4$) and concentrated in vacuo. Pure E1 was obtained by flash chromatography, eluting with 25% EtOAc in hexanes in a yield of 200 mg (46%). The $^1$H NMR was consistent with that of the desired structure.

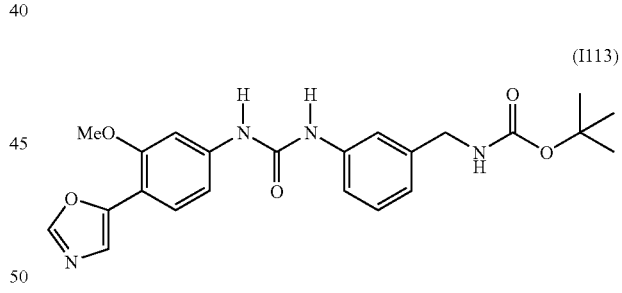
(I113)

A solution of C4 (150 mg, 0.789 mmole) and 1,1-dicarbonylimidiazole (160 mg, 0.986 mmole) were combined in THF (5 mL) and stirred for 6 hours at ambient temperature. The precipitation of imidazole was noted. To this was then added E1 (351 mg, 1.58 mmole) and N,N-dimethylaminopyridine (97 mg, 0.789 mmole) and the mixture was refluxed overnight, resulting in a homogenous solution. Upon cooling to ambient temperature, the reaction was diluted with EtOAc (20 mL), washed with KHSO$_4$(aq), water, and brine, dried (MgSO$_4$) and concentrated. Pure I113 was obtained through flash chromatography, eluting with a gradient of 20–30–35% acetone in hexanes in a yield of 164 mg (47%). $^1$H NMR (500 MHz, d$_6$-DMSO) δ 8.90 (s), 8.75 (s), 8.38 (s), 7.60 (d), 7.51 (s), 7.3–7.46 (m), 7.21–7.27 (t), 7.05 (dd), 6.87 (d), 4.12 (d), 3.93 (s), 1.44 (s). R$_f$ 0.21 (5% MeOH/CH$_2$Cl$_2$).

C. Synthesis of Compound I168

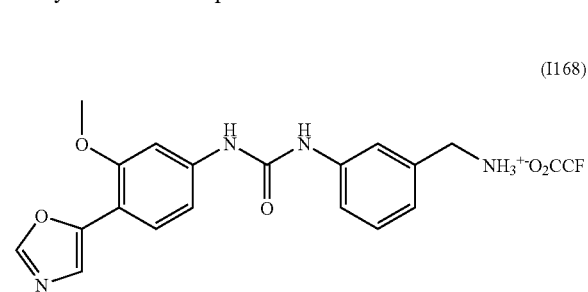
(I168)

A suspension of I113 (250 mg, 5.76 mmol) in CH$_2$Cl$_2$ (1 mL) was treated in a dropwise fashion at ambient temperature with several equivalents of trifluoroacetic acid and stirred for 90 min. The resulting solution was stripped in vacuo and titrated with CH$_2$Cl$_2$ and methanol. Pure product I168 was isolated by filtration in a yield of 258 mg (99%). The $^1$H NMR was consistent with that of the desired product.

D. Synthesis of Compound 41

To a room temperature solution of 1-methoxy-2-propanol (75 mg, 832 μmole) in THF (1.0 mL) was added solid 1,1'-carbonyl diimidazole (121 mg, 749 μmole) in one portion. The resulting mixture was stirred at room temperature overnight, then treated sequentially with TEA (174 μL, 1.25 mmole), solid compound I168 (376 mg, 832 μmole), and DMF (1.0 mL). The resulting solution was stirred at room temperature for one day, then diluted with ethyl acetate, washed sequentially with water and brine, dried over MgSO$_4$, filtered, and concentrated in vacuo. The crude product was then purified by flash chromatography (silica gel, 97.5/1.5 CH$_2$Cl$_2$). The chromatographed product was then triturated with a 9/1 mixture of ethyl ether/ethyl acetate to give compound 45 (65 mg, 56% yield) as a white, powdery solid.

1H NMR (500 MHz, acetone-d6): 8.34 (s, 1H); 8.21 (s, 1H); 8.12 (s, 1H); 7.67 (s, 1H); 7.65 (dd, 1H); 7.50 (d, 1H); 7.47 (d, 1H); 7.43 (s, 1H); 7.25 (dd, 1H); 7.10 (dd, 1H); 6.97 (d, 1H); 6.68 (m, 1H); 4.92 (m, 1H); 4.32 (d, 2H); 4.01 (s, 3H); 3.43 (dd, 1H); 3.33 (dd, 1H); 3.31 (s, 3H); 1.18 (d, 3H).

Other compounds of this invention may be prepared in a similar manner substituting the appropriate alcohol for 1-methoxy-2-propanol [i.e., HO—CH(R$_1$)(R$_2$)] in step C.

EXAMPLE 2

Preparation of Compound 169

A. Preparation of the Left Hand Side Coupling Intermediate (R$_{10}$=Cyano):

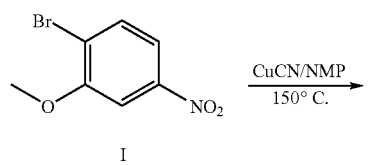
I

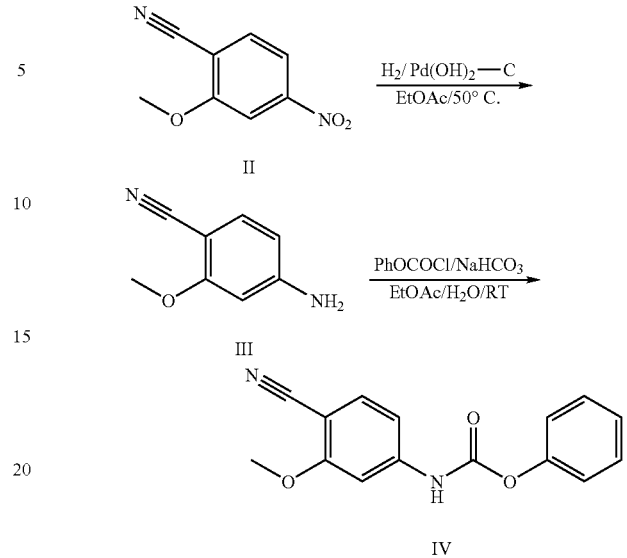

Copper(I)cyanide (7.2 g, 80.8 mmole) was combined with 2-bromo-5-nitroanisole (I) (15 g, 64.6 mmole) in NMP (70 mL) and heated to 150° C. overnight under an N$_2$ atmosphere. The mixture was treated with Celite, cooled to room temperature, then diluted with EtOAc and 1.0 N NaOH and allowed to stir for 15 minutes. The heterogeneous mixture was filtered through a pad of Celite with EtOAc, the phases were separated, and the aqueous phase was washed 3 times with EtOAc. The combined organics were washed sequentially with 1.0 N NaOH, water, and brine, then dried over Na$_2$SO$_4$, filtered and concentrated in vacuo. The crude product was dissolved in CH$_2$Cl$_2$, filtered through a short pad of silica gel to remove solids and most colored impurities, then concentrated in vacuo to give II (10.41 g, 90%) as a brownish-orange solid.

$^1$H NMR (500 MHz, CDCl$_3$): 7.90 (d, 1H); 7.84 (s, 1H); 7.77 (d, 1H); 4.07 (s, 3H).

To a room temperature solution of II (7.2 g, 40.4 mmoles) in EtOAc-EtOH (220–15 mL) was added 10% Pd/C (1.8 g) resulting in a heterogeneous black mixture. The reaction was placed under 1 atmosphere (balloon) of H$_2$. warmed to 50° C., and stirred overnight. Reaction was cooled to room temperature, the catalyst was removed via filtration, and the filtrate was concentrated in vacuo to give III (5.56 g, 93%) as a crystalline solid.

$^1$H NMR (500 MHz, CDCl$_3$): 7.29 (d, 1H); 6.22 (d, 1H); 6.17 (s, 1H); 4.20 (broad s, 2H); 3.85 (s, 3H).

To a room temperature, biphasic mixture of phenyl chloroformate (1.6 mL, 12.82 mmoles) in EtOAc (20 mL) and sat. NaHCO$_3$ (~1M, 16 mL) was added III (950 mg, 6.41 mmoles) as a solution in EtOAc (10 mL) over a 10 minute period. The resulting heterogeneous mixture was stirred at room temperature for 30 minutes and then the phases were separated. The organic phase was washed with brine, dried over Na$_2$SO$_4$, filtered through a pad of silica gel with EtOAc, and concentrated in vacuo to give a thick oil. The resulting oil was diluted in toluene (30 mL) and treated with hexanes (30 mL) resulting in a thick precipitate. This mixture was stirred for 30 minutes, filtered, solids washed with 1:1 toluene:hexanes, then hexanes alone, and dried to constant weight under high vacuum to give IV (1.65 g, 96%) as a white powder.

$^1$H NMR (500 MHz, dmso-d6); 10.76 (s, 1H); 7.69 (d, 1H); 7.44 (d, 1H); 7.40 (d, 1H); 7.26 (m, 3H); 7.15 (d, 1H); 3.85 (s, 3H).

B. Preparation of the Right Hand Side Coupling Intermediate ($R_9$=S-methyl):

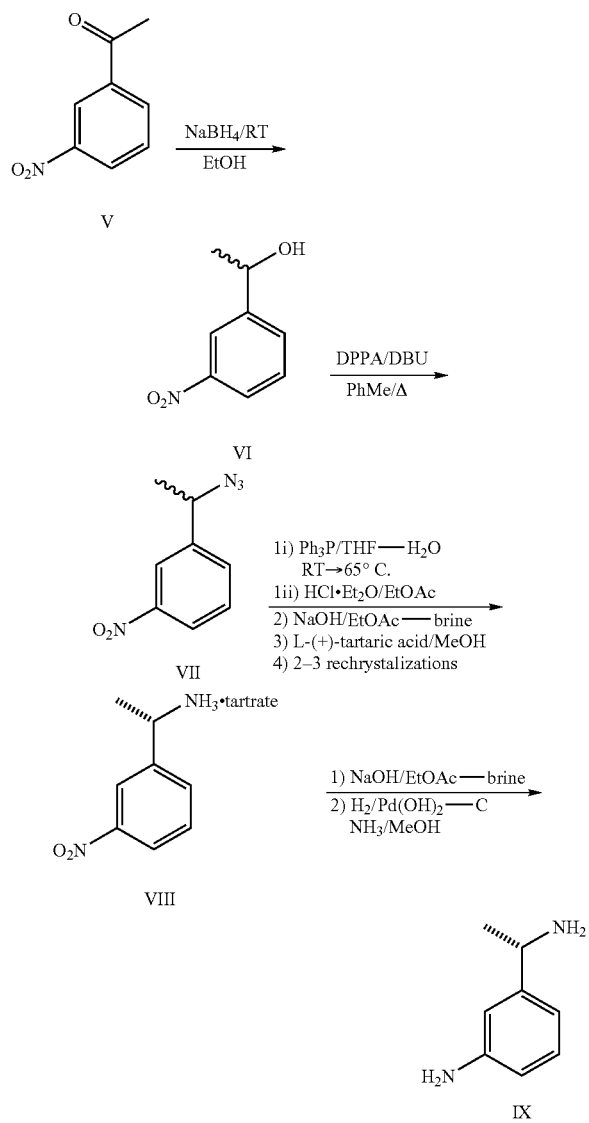

To a room temperature solution of V (200 g, 1.21 moles) in EtOH (2 L) was added NaBH$_4$ (50.3 g, 1.33 moles) portionwise over 30 minutes, not allowing the internal temperature to rise over 40° C. The reaction was allowed to stir at room temperature for 4 hours. It was then quenched with water (~100 mL), concentrated in vacuo, diluted with EtOAc, washed twice with water, once with sat. NaHCO$_3$, dried over MgSO$_4$, filtered, and concentrated in vacuo to give VI (191.7 g, 95%) as a yellowish power.

$^1$H NMR (500 MHz, CDCl$_3$): 8.21 (s, 1H); 8.09 (d, 1H); 7.70 (d, 1H); 7.49 (dd, 1H); 5.01 (dd, 1H); 2.45 (s, 1H); 1.52 (d, 3H).

To a room temperature solution of VI (181 g, 1.08 moles) was added DPPA (250 mL, 1.16 moles) at a rate slow enough to keep the reaction temperature under 45° C. Once the addition of DPPA was complete, the mixture was treated with DBU (177 mL, 1.18 moles) at a rate slow enough to keep the reaction temperature under 45° C. Upon complete addition, the reaction was warmed to 60° C. and maintained at that temperature overnight. The resulting biphasic mixture was cooled to room temperature, washed sequentially with water, then 0.5 M HCl. The organic phase was dried over Na$_2$SO$_4$, filtered, and concentrated in vacuo to give a yellow-green oil that was not purified further.

$^1$H NMR (500 MHz, CDCl$_3$): 8.21 (s, 1H); 8.18 (d, 1H); 7.68 (d, 1H); 7.56 (q, 1H); 4.76 (dd, 1H); 1.59 (d, 3H).

To a room temperature solution of VII (8.17 g, 42.51 μmoles) in THF-water (80 mL–10 mL) was added Ph$_3$P (12.3 g, 46.76 mmoles) as a solution in THF (20 mL) over a 10 minute period. Nitrogen evolution was immediate and constant throughout the addition. The reaction was then heated to 65° C. overnight, then cooled to room temperature. The crude mixture was concentrated in vacuo, diluted with EtOAc, washed with brine, dried over Na$_2$SO$_4$, and filtered. The resulting filtrate was treated with 1 N HCl/Et$_2$O at room temperature over a 10 minute period resulting in precipitate formation. The mixture was stirred at room temperature for 15 minutes, then filtered. The solids were washed with Et$_2$O to give a yellow powder. The crude amine hydrochloride salt was suspended in brine/EtOAc, and treated with 10 N NaOH (5 mL, 50 mmoles) at room temperature. The resulting mixture was stirred at room temperature until all solids were dissolved. The phases were separated, the aqueous phase was washed with EtOAc twice, the combined organic phases were washed with brine, dried over Na$_2$SO$_4$, filtered, and concentrated in vacuo. The crude amine was diluted in MeOH (50 mL) and added to a refluxing solution of L-(+)-tartaric acid (5.33 g, 35.33 mmoles) in MeOH (450 mL). A precipitate formed immediately and was then dissolved in the MeOH mixture upon refluxing for 15 minutes. The internal temperature was lowered to 50° C. and maintained there overnight. The internal temperature was then lowered to 30° C. and maintained for another 24 hours followed by another 24 hours at room temperature. The resulting crystals (spikes) were filtered, washed with MeOH and Et$_2$O, and the mother liquor discarded. The resulting crystals were dissolved in 200 mL of refluxing MeOH, cooled slowly as described above, filtered, and washed with MeOH, then Et$_2$O to give the first crop of VIII (2.21 g, 20%) as a white solid. The mother liquor was concentrated in vacuo, solids dissolved in 50 mL of refluxing MeOH, cooled as above, filtered, and washed with MeOH and Et$_2$O to give a second crop of VIII (1.50 g, 13%) as a white solid. The optical purity was determined on the corresponding phenyl carbamate of each crop to be >97% ee.

Enantiomeric excesses were determined using a Chiralcel OD column (0.46 cm×25 cm) made by Daicel Chemical Industries and purchased from Chiral Technologies. The mobile phase employed was a 70:30 hexane:IPA mixture in an isocratic run out to 65 minutes at 0.8 ml/min flow rate using a 3–4 μl injection of a 1–2 mg/ml solution of the phenyl carbamate dissolved in above mentioned hexane:IPA mixture. The desired S-methyl enantiomer elutes first at ~47.2 minutes while the undesired R-methyl enatiomer comes off at ~51.7 minutes while monitoring at 214, 254, 280 nm wavelength.

All samples were run on a Hewlett Packard Series 1050 HPLC with a diode array detector.

To a heterogeneous suspension of VIII (1.11 g, 3.51 mmoles) in EtOAc (20 mL) and brine (20 mL) was added 10 N NaOH (0.77 mL, 7.72 mmoles) at room temperature. The resulting mixture was stirred at room temperature until all salts had dissolved. The phases were then separated, and the aqueous phase washed with EtOAc. The combined organic phases were washed with brine, dried over Na$_2$SO$_4$, filtered, and concentrated in vacuo. The crude nitro-benzylamine was diluted in 7M NH$_3$-MeOH (20 mL), 20% Pd(OH)$_2$—C added, and placed under 45 psi of H$_2$ for 5 hours. The resulting mixture was filtered to remove the catalyst, concentrated in vacuo, azeotroped once with CH$_2$Cl$_2$, then placed under high vacuum to give IX (455 mg, 95%) as a waxy white solid.

$^1$H NMR (500 MHz, dmso-d6): 6.91 (dd, 1H); 6.56 (s, 1H); 6.50 (d, 1H); 6.38 (d, 1H); 4.90 (broad s, 2H); 3.82 (q, 1H); 3.31 (broad s, 2H); 1.18 (d, 3H).

C. Preparation of Compound 169

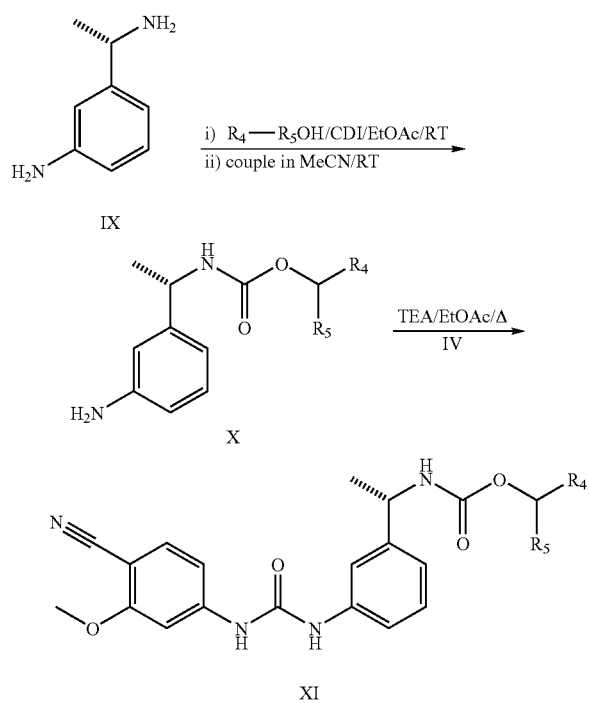

To a room temperature solution of 3-(R)-hydroxy pentanitrile (212 mg, 2.14 mmoles) was added CDI (521 mg, 3.21 mmoles) in one portion. The resulting mixture was stirred at room temperature for 1 hour, then treated with solid silica gel. The heterogeneous mixture was stirred vigorously for 10 minutes, filtered through a short pad of silica gel with 4:1 EtOAc:IPA, concentrated in vacuo, azeotroped twice with MeCN, then combined with IX (350 mg, 2.57 mmoles) in MeCN (2 mL) and stirred at room temperature for 1 day. The resulting mixture was diluted with EtOAc, washed with water and then brine, dried over Na$_2$SO$_4$, filtered, concentrated, and flash chromatographed (silica gel, 1/2?1/3?0/1 hexanes/EtOAc?4/1 EtOAc/IPA) to give X (472 mg, 84%) as a clear, thick oil.

$^1$H NMR (500 MHz, dmso-d6): 7.73 (d, 1H); 6.94 (dd, 1H); 6.51 (s, 1H); 6.47 (d, 1H); 6.38 (d, 1H); 4.98 (broad s, 2H); 4.67 (m, 1H); 4.49 (m, 1H); 2.82 (m, 2H); 1.62 (m, 2H); 1.27 (d, 3H); 0.89 (dd, 3H).

To a room temperature solution of X (470 mg, 1.80 mmoles) in EtOAc (5 mL) was added IV (440 mg, 1.63 mmoles) and TEA (0.23 mL, 1.63 mmoles). The resulting mixture was heated to reflux and stirred at that temperature for 6 hours. The resulting crude mixture was cooled to room temperature, diluted with EtOAc, washed with brine/1N HCl, followed by brine alone, dried over Na$_2$SO$_4$, filtered, concentrated in vacuo, and flash chromatographed (silica gel, 1/1?1/2?1/3?1/4?0/1 hexanes/EtOAc?4/1 EtOAc/IPA) to give 169 (740 mg, 100%) as a white, foamy solid.

$^1$H NMR (500 MHz, dmso-d6): 9.21 (s, 1H); 8.84 (s, 1H); 7.93 (d, 1H); 7.59 (d, 1H); 7.51 (s, 1H); 7.41 (s, 1H); 7.29 (d, 1H); 7.23 (dd, 1H); 7.01 (d, 1H); 6.92 (d, 1H); 4.69 (m, 1H); 4.63 (m, 1H); 3.89 (s, 3H); 2.82 (m, 2H); 2.62 (m, 2H); 1.31 (d, 3H); 0.90 (t, 3H)

EXAMPLE 3

IMPDH Activity Inhibition Assay

IMP dehydrogenase activity was assayed following an adaptation of the method first reported by Magasanik. [B. Magasanik et al., *J. Biol. Chem.*, 226, p. 339 (1957), the disclosure of which is herein incorporated by reference]. Enzyme activity was measured spectrophotometrically., by monitoring the increase in absorbance at 340 nm due to the formation of NADH (?340 is 6220 M$^{-1}$ cm$^{-1}$). The reaction mixture contained 0.1 M potassium phosphate 8.0, 0.5 mM EDTA, 2 mM DTT, 200 μM IMP and enzyme (IMPDH human type II) at a concentration of 15 to 50 nM. This solution is incubated at 37° C. for 10 minutes. The reaction is started by adding NAD to a final concentration of 200 μM and the initial rate is measured by following the linear increase in absorbance at 340 nm for 10 minutes. For reading in a standard spectrophotometer (path length 1 cm) the final volume in the cuvette is 1.0 ml. The assay has also been adapted to a 96 well microtiter plate format; in this case the concentrations of all the reagents remain the same and the final volume is decreased to 200 μl.

For the analysis of inhibitors, the compound in question is dissolved in DMSO to a final concentration of 20 mM and added to the initial assay mixture for preincubation with the enzyme at a final volume of 2–5% (v/v). The reaction is started by the addition of NAD, and the initial rates measured as above. K$_i$ determinations are made by measuring the initial velocities in the presence of varying amounts of inhibitor and fitting the data using the tight-binding equations of Henderson (Henderson, P. J. F. (1972) Biochem. J. 127, 321].

These results are shown in Table 2. Category "A" indicates a K$_I$ of 10 nM or less, category "B" indicates a K$_I$ of greater than 10 and less than 50 nM, category "C" indicates a K$_I$ of 50 nM or greater, "ND" indicates inhibitory activity was not determined.

TABLE 2

IMPDH inhibitory activity.

| Cmpd | Ki (nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |

TABLE 2-continued

IMPDH inhibitory activity.

| Cmpd | Ki (nM) |
|---|---|
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | B |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | ND |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | B |
| 82 | C |
| 83 | B |
| 84 | B |
| 85 | C |
| 86 | B |
| 87 | A |
| 88 | A |
| 89 | A |
| 90 | A |
| 91 | A |
| 92 | A |
| 93 | B |
| 94 | A |
| 95 | B |
| 96 | B |
| 97 | B |
| 98 | B |
| 99 | B |
| 100 | B |
| 101 | A |
| 102 | A |
| 103 | C |
| 104 | B |
| 105 | A |
| 106 | C |
| 107 | C |
| 108 | C |
| 109 | C |
| 110 | C |
| 111 | C |
| 112 | C |
| 113 | C |
| 114 | C |
| 115 | C |
| 116 | C |
| 117 | C |
| 118 | C |
| 119 | C |
| 120 | C |
| 121 | ND |
| 122 | C |
| 123 | C |
| 124 | C |
| 125 | C |
| 126 | C |
| 127 | C |
| 128 | C |
| 129 | C |
| 130 | C |
| 131 | C |
| 132 | C |
| 133 | B |
| 134 | B |
| 135 | C |
| 136 | C |
| 137 | C |
| 138 | A |
| 139 | C |
| 140 | C |
| 141 | B |
| 142 | B |
| 143 | ND |
| 144 | ND |
| 145 | ND |
| 146 | ND |
| 147 | ND |
| 148 | ND |
| 149 | ND |
| 150 | ND |
| 151 | ND |
| 152 | ND |
| 153 | ND |
| 154 | ND |
| 155 | ND |
| 156 | ND |
| 157 | B |
| 158 | B |
| 159 | A |
| 160 | C |
| 161 | A |
| 162 | B |

TABLE 2-continued

IMPDH inhibitory activity.

| Cmpd | Ki (nM) |
|---|---|
| 163 | B |
| 164 | B |
| 165 | C |
| 166 | C |
| 167 | C |
| 168 | B |
| 169 | A |
| 170 | A |
| 171 | C |
| 172 | C |
| 172 | C |
| 173 | C |
| 174 | C |
| 175 | C |
| 176 | C |
| 177 | C |
| 178 | C |
| 179 | C |
| 180 | B |
| 181 | A |
| 182 | C |
| 183 | B |
| 184 | B |
| 185 | B |
| 186 | C |
| 187 | B |

Other compounds of this invention will also have IMPDH inhibitory activity.

EXAMPLE 4

Cellular Assays

A. Isolation of peripheral blood mononuclear cells (PB-MCs): Human venous blood was drawn from normal healthy volunteers using heparin as an anti-coagulant. PBMCs were isolated from blood by centrifugation over Ficoll-paque gradient or CPT tubes (Becton-Dickinson) using standard conditions. PBMCs were harvested, washed and re-suspended in complete RPMI, counted and diluted to $1 \times 10^6$ cells/mL.

B. PBMC and Splenocyte Proliferation Assays:

$5 \times 10^4$ cells (for human PBMC T cells) or $1 \times 10^5$ cells (for human PBMC B cells) were added per well of a 96-well plate. For T-cell assays, phyto-hemagglutinin (PHA) was added to a final concentration of 10–20 µg/mL per well for cell. For B-cell assays, *Staphylococcal* protein A (SPAS) was added to a final concentration of 2 µg/mL per well.

Serial 4-fold dilutions of inhibitor stocks were made in complete RPMI and added to cells such that the final concentration of compounds ranged from 20 µM to 20 nM, while DMSO was maintained at a final concentration of 0.1%. The cells were then incubated for 3 days. All samples were tested in triplicate. Tritiated thymidine (0.4 µCi/well) was added for the last 24 hours of the assay. The cells were harvested onto Betaplate filters and counted in a scintillation counter. Concentrations of compounds required to inhibit proliferation of cells by 50% (IC50 values) were calculated using the SoftMax Pro™ (Molecular Devices) computer software package.

The results of these assays are shown in Table 3. Category "A" indicates a $IC_{50}$ of 100 nM or less, category "B" indicates a $IC_{50}$ of greater than 100 and less than 1000 nM, category "C" indicates a $IC_{50}$ of 1000 nM or greater, "ND" indicates inhibitory activity was not determined in the indicated cellular assay.

TABLE 3

Cellular Activity

| Cmpd | T-cells (IC50) | B-cells (IC50) |
|---|---|---|
| 1 | B | A |
| 2 | B | B |
| 3 | B | B |
| 4 | C | C |
| 5 | C | C |
| 6 | B | B |
| 7 | B | B |
| 8 | B | B |
| 9 | B | B |
| 10 | B | C |
| 11 | C | B |
| 12 | B | B |
| 13 | B | B |
| 14 | C | B |
| 15 | B | B |
| 16 | C | C |
| 17 | C | C |
| 18 | C | C |
| 19 | B | B |
| 20 | B | B |
| 21 | B | C |
| 22 | B | B |
| 23 | A | A |
| 24 | C | C |
| 25 | B | B |
| 26 | A | A |
| 27 | A | A |
| 28 | B | B |
| 29 | A | A |
| 30 | C | B |
| 31 | ND | ND |
| 32 | B | A |
| 33 | B | B |
| 34 | C | B |
| 35 | B | B |
| 36 | C | C |
| 37 | B | B |
| 38 | B | B |
| 39 | B | B |
| 40 | C | B |
| 41 | B | B |
| 42 | B | B |
| 43 | B | B |
| 44 | B | B |
| 45 | B | B |
| 46 | B | B |
| 47 | B | B |
| 48 | B | B |
| 49 | B | B |
| 50 | C | C |
| 51 | B | B |
| 52 | C | C |
| 53 | ND | ND |
| 54 | ND | ND |
| 55 | ND | ND |
| 56 | ND | B |
| 57 | B | B |
| 58 | B | B |
| 59 | C | B |
| 60 | B | B |
| 61 | B | B |
| 62 | B | B |
| 63 | B | B |
| 64 | ND | ND |
| 65 | B | B |
| 66 | C | C |
| 67 | B | B |
| 68 | B | B |
| 69 | B | B |
| 70 | C | C |

TABLE 3-continued

| Cmpd | Cellular Activity T-cells (IC50) | B-cells (IC50) |
|---|---|---|
| 71 | C | C |
| 72 | B | B |
| 73 | C | C |
| 74 | C | C |
| 75 | B | B |
| 76 | A | A |
| 77 | B | B |
| 78 | B | B |
| 79 | B | B |
| 80 | B | B |
| 81 | B | B |
| 82 | B | B |
| 83 | B | B |
| 84 | B | B |
| 85 | ND | ND |
| 86 | C | C |
| 87 | A | A |
| 88 | B | B |
| 89 | A | A |
| 90 | B | B |
| 91 | C | C |
| 92 | B | B |
| 93 | ND | ND |
| 94 | ND | ND |
| 95 | ND | ND |
| 96 | ND | ND |
| 97 | A | A |
| 98 | B | B |
| 99 | B | B |
| 100 | B | B |
| 101 | A | A |
| 102 | B | B |
| 103 | B | A |
| 104 | A | A |
| 105 | B | B |
| 106 | A | A |
| 107 | B | B |
| 108 | B | A |
| 109 | B | B |
| 110 | B | A |
| 111 | B | B |
| 112 | C | C |
| 113 | C | C |
| 114 | C | C |
| 115 | C | C |
| 116 | C | C |
| 117 | C | C |
| 118 | B | B |
| 119 | B | B |
| 120 | C | C |
| 121 | ND | ND |
| 122 | C | C |
| 123 | C | C |
| 125 | B | B |
| 126 | C | C |
| 127 | C | C |
| 128 | B | B |
| 129 | B | B |
| 130 | B | C |
| 131 | B | B |
| 132 | B | B |
| 133 | ND | ND |
| 134 | B | B |
| 135 | ND | ND |
| 136 | ND | ND |
| 137 | ND | ND |
| 138 | B | B |
| 139 | ND | ND |
| 140 | ND | ND |
| 141 | ND | ND |
| 142 | ND | ND |
| 143 | ND | ND |
| 144 | ND | ND |
| 145 | ND | ND |
| 146 | ND | ND |
| 147 | ND | ND |
| 148 | ND | ND |
| 149 | ND | ND |
| 150 | ND | ND |
| 151 | ND | ND |
| 152 | ND | ND |
| 153 | ND | ND |
| 154 | ND | ND |
| 155 | ND | ND |
| 156 | ND | ND |
| 157 | A | A |
| 158 | C | B |
| 159 | B | B |
| 160 | ND | ND |
| 161 | ND | ND |
| 162 | B | B |
| 163 | A | A |
| 164 | B | B |
| 165 | ND | ND |
| 166 | B | B |
| 167 | ND | ND |
| 168 | B | B |
| 169 | A | A |
| 170 | B | B |
| 171 | B | A |
| 172 | C | C |
| 173 | C | B |
| 174 | C | B |
| 175 | C | C |
| 176 | C | C |
| 177 | ND | ND |
| 178 | ND | ND |
| 179 | C | C |
| 180 | B | C |
| 181 | A | A |
| 182 | C | B |
| 183 | B | B |
| 184 | B | B |
| 185 | B | B |
| 186 | ND | ND |
| 187 | B | A |

EXAMPLE 5

Anti-Viral Assays

The anti-viral efficacy of compounds may be evaluated in various in vitro and in vivo assays. For example, compounds may be tested in in vitro viral replication assays. In vitro assays may employ whole cells or isolated cellular components. In vivo assays include animal models for viral diseases. Examples of such animal models include, but are not limited to, rodent models for HBV or HCV infection, the Woodchuck model for HBV infection, and chimpanzee model for HCV infection.

While we have hereinbefore presented a number of embodiments of this invention, it is apparent that our basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:
1. A compound of formula (A):

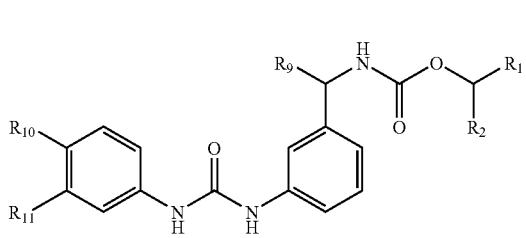

wherein:
each of $R_1$ and $R_2$ is independently selected from hydrogen, —$CF_3$; —($C_1$–$C_6$)-straight or branched alkyl; —($C_2$–$C_6$)-straight or branched alkenyl or alkynyl; —($C_1$–$C_6$)-straight or branched alkyl-$R_7$; -[($C_2$–$C_6$)-straight or branched alkenyl or alkynyl]-$R_7$ or —$R_7$; and wherein at least one of $R_1$ or $R_2$ is —($C_1$–$C_6$)-straight or branched alkyl-$R_7$; -[($C_2$–$C_6$)-straight or branched alkenyl or alkynyl]-$R_7$ or —$R_7$;
wherein up to 4 hydrogen atoms in any of said alkyl, alkenyl or alkynyl are optionally and independently replaced by $R_3$; and
wherein one or both of $R_1$ or $R_2$ are optionally esterified to form a prodrug; or
each $R_3$ is independently selected from halo, CN, —$OR_4$, or —$N(R_5)_2$;
$R_4$ is selected from hydrogen, —($C_1$–$C_6$)-straight or branched alkyl, —($C_2$–$C_6$)-straight or branched alkenyl or alkynyl, -[($C_1$–$C_6$)-straight or branched alkyl]-$R_7$, -[($C_2$–$C_6$)-straight or branched alkenyl or alkynyl]-$R_7$, —C(O)-[($C_1$–$C_6$)-straight or branched alkyl], —C(O)-[-($C_2$–$C_6$)-straight or branched alkenyl or alkynyl], —C(O)-[($C_1$–$C_6$)-straight or branched alkyl]-N($R_8$)$_2$, —C(O)-[($C_2$–$C_6$)-straight or branched alkenyl or alkynyl]-N($R_8$)$_2$, —P(O)(OR$_8$)$_2$, —P(O)(OR$_8$)(R$_8$), —C(O)—$R_7$, —S(O)$_2$N(R$_5$)$_2$, -[($C_1$–$C_6$)-straight or branched alkyl]-CN, or -[($C_2$–$C_6$)-straight or branched alkenyl or alkynyl]-CN;
each $R_5$ is independently selected from hydrogen, —($C_1$–$C_6$)-straight or branched alkyl, ($C_2$–$C_6$)-straight or branched alkenyl or alkynyl, -[($C_1$–$C_6$)-straight or branched alkyl]-$R_7$, -[($C_2$–$C_6$)-straight or branched alkenyl or alkynyl]-$R_7$, -[($C_1$–$C_6$)-straight alkyl]-CN, -[($C_2$–$C_6$)-straight or branched alkenyl or alkynyl]-CN, -[($C_1$–$C_6$)-straight or branched alkyl]-OR$_4$, -[($C_2$–$C_6$)-straight or branched alkenyl or alkynyl]-OR$_4$, —C(O)—($C_1$–$C_6$)-straight or branched alkyl, —C(O)-[(($C_2$–$C_6$)-straight or branched alkenyl or alkynyl], —C(O)—$R_7$, —C(O)O—$R_7$, —C(O)O—($C_1$–$C_6$)-straight or branched alkyl, —C(O)O-[($C_2$–$C_6$)-straight or branched alkenyl or alkynyl], —S(O)$_2$—($C_1$–$C_6$)-straight or branched alkyl, or —S(O)$_2$—$R_7$;
each $R_7$ is a monocyclic or bicyclic ring system wherein in said ring system:
  i. each ring comprises 3 to 7 ring atoms;
  ii. any $CH_2$ is optionally replaced with C(O);
each $R_8$ is independently selected from hydrogen or -[$C_1$–$C_4$]-straight or branched alkyl;
wherein in any ring system in said compound up to 3 hydrogen atoms bound to the ring atoms are optionally and independently replaced with halo, hydroxy, nitro, cyano, amino, ($C_1$–$C_4$)-straight or branched alkyl; O—($C_1$–$C_4$)-straight or branched alkyl, ($C_{2-C4}$)-straight or branched alkenyl or alkynyl, or O—($C_2$–$C_6$)-straight or branched alkenyl or alkynyl; and
wherein any ring system is optionally benzofused;
$R_9$ is selected from (R)-methyl, (S)-methyl, (R)-ethyl, (S)-ethyl, (R)-hydrocymethyl or (S)-hydroxymethyl;
$R_{10}$ is —C≡N; and
$R_{11}$ is selected from halo, —O—($C_1$–$C_3$) straight alkyl, or —O—($C_2$–$C_3$) straight alkenyl or alkynyl.

2. The compound according to claim 1, wherein $R_9$ is (S)-methyl.

3. The compound according to claim 1, wherein $R_{11}$ is selected from O-methyl, O-ethyl or O-isopropyl.

4. The compound according to claim 1, wherein one of $R_1$ or $R_2$ is selected from hydrogen, ethyl or phenyl; and the other of $R_1$ or $R_2$ is selected from —$CH_2OH$, —$CH_2CN$, —$CH_2CH_2CN$ or $CH_2N(CH_2CH_3)_2$.

5. A pharmaceutical composition comprising a compound according to claim 1 in an amount effective to inhibit IMPDH and a pharmaceutically acceptable carrier, adjuvant or vehicle.

6. The pharmaceutical composition according to claim 5, comprising a compound in an amount effective to inhibit IMPDH and a pharmaceutically acceptable carrier, adjuvant or vehicle, wherein said compound is selected from:

162

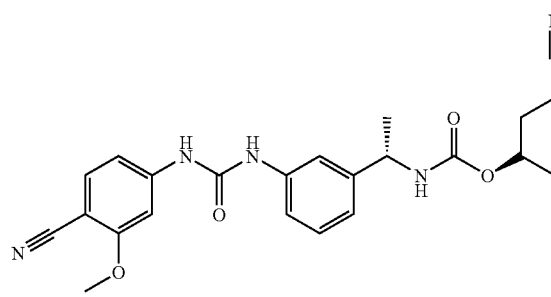

168

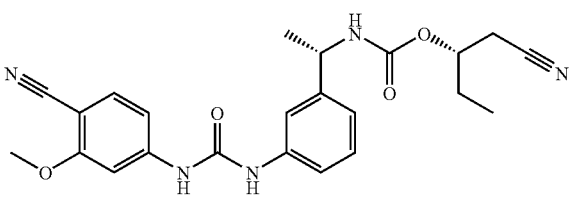

169

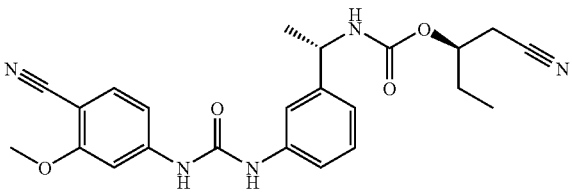

170

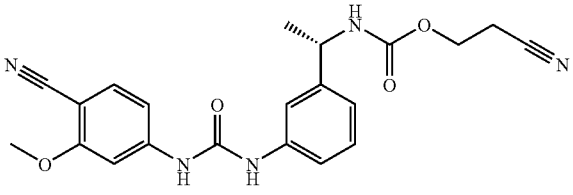

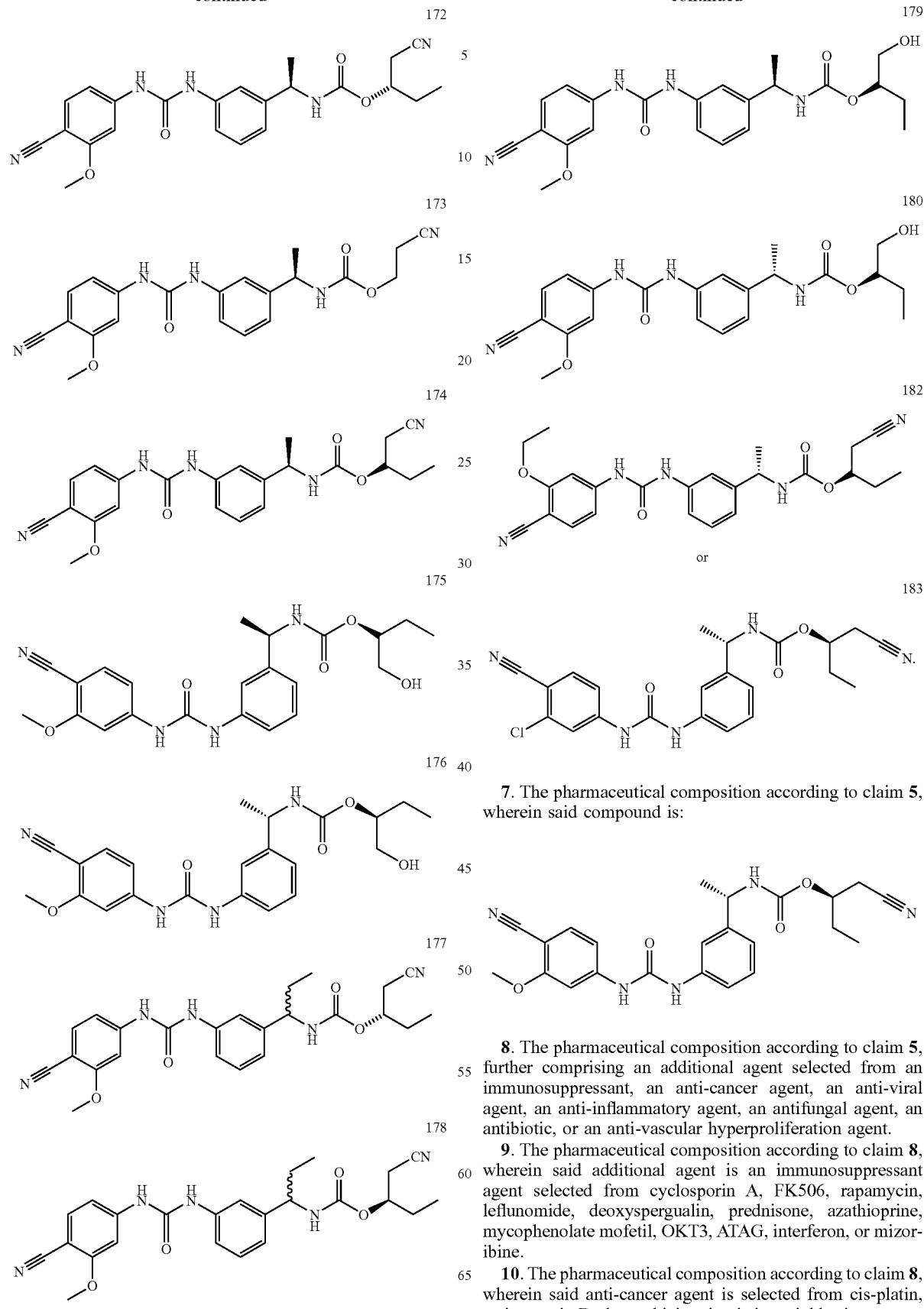

7. The pharmaceutical composition according to claim 5, wherein said compound is:

8. The pharmaceutical composition according to claim 5, further comprising an additional agent selected from an immunosuppressant, an anti-cancer agent, an anti-viral agent, an anti-inflammatory agent, an antifungal agent, an antibiotic, or an anti-vascular hyperproliferation agent.

9. The pharmaceutical composition according to claim 8, wherein said additional agent is an immunosuppressant agent selected from cyclosporin A, FK506, rapamycin, leflunomide, deoxyspergualin, prednisone, azathioprine, mycophenolate mofetil, OKT3, ATAG, interferon, or mizoribine.

10. The pharmaceutical composition according to claim 8, wherein said anti-cancer agent is selected from cis-platin, actinomycin D, doxorubicin, vincristine, vinblastine, etoposide, amsacrine, mitoxantrone, tenipaside, taxol, colchicine, cyclosporin A, phenothiazines, interferon or thioxantheres.

11. The pharmaceutical composition according to claim 8, wherein said anti-viral agent is selected from Cytovene, Ganciclovir, trisodium phosphonoformate, Ribavirin, d4T, ddT, AZT, and acyclovir.

12. The pharmaceutical composition according to claim 8, wherein said anti-vascular hyperproliferation agent is selected from HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin or 5-(3'-pyridinylmethyl)benzofuran-2-carboxylate.

13. A method of treating an IMPDH-mediated disease or condition in a mammal comprising the step of administrating to said mammal a pharmaceutical composition according to claim 5 or claim 7.

14. The method according to claim 13, wherein said IMPDH-mediated disease or condition is selected from transplant rejection, graft versus host disease, or an autoimmune disease.

15. The method according to claim 13, wherein said mammal is administered an additional immunosuppressant in a separate dosage form or as part of said composition, wherein said immunosuppressant is selected from cyclosporin A, FK506, rapamycin, leflunomide, deoxyspergualin, prednisone, azathioprine, mycophenolate mofetil, OKT3, ATAG, interferon, or mizoribine.

16. A method for inhibiting viral replication in a mammal comprising the step of administering to said mammal a pharmaceutical composition according to claim 5 or claim 7.

17. The method according to claim 16, wherein said mammal is suffering from a viral infection caused by a virus selected from orthomyxovirus, paramyxovirus, herpesvirus, retrovirus, flavivirus, pestivirus, hepatotrophic virus, bunyavirus, Hantaan virus, Caraparu virus, human papilloma virus, encephalitis virus, arena virus, reovirus, vesicular stomatitis virus, rhinovirus, enterovirus, Lassa fever virus, togavirus, poxvirus, adenovirus, rubiola, or rubella.

18. The method according to claim 16, wherein said mammal is administered an additional anti-viral agent in a separate dosage form or as part of said pharmaceutical composition.

19. A method for inhibiting vascular cellular hyperproliferation in a mammal comprising the step of administering to said mammal a pharmaceutical composition according to claim 5 or claim 7.

20. The method according to claim 19, wherein said method is useful in treating restenosis, stenosis, artherosclerosis or other hyperproliferative vascular disease.

21. The method according to claim 19, wherein said mammal is administered an additional anti-vascular hyperproliferative agent in a separate dosage form or as part of said pharmaceutical composition.

22. A method for inhibiting tumors and cancer in a mammal, wherein said tumors and cancer are mediated by IMPDH, comprising the step of administering to said mammal a pharmaceutical composition according to claim 5 or claim 7.

23. The method according to claim 22, wherein said method is useful to treat lymphoma, leukemia and other forms of cancer.

24. The method according to claim 23, wherein said mammal is administered an additional anti-tumor or anti-cancer agent in a separate dosage form or as part of said pharmaceutical composition.

25. A method for inhibiting inflammation or an inflammatory disease in a mammal comprising the step of administering to said mammal a pharmaceutical composition according to claim 5 or claim 7.

26. The method according to claim 25, wherein said method is useful for treating osteoarthritis, acute pancreatitis, chronic pancreatitis, asthma or adult respiratory distress syndrome.

27. The method according to claim 26, wherein said mammal is administered an additional anti-inflammatory agent in a separate dosage form or as part of said pharmaceutical composition.

28. The compound according to claim 1, wherein:
at least one of $R_1$ or $R_2$ is selected from hydrogen, methyl, ethyl, n-propyl, isopropyl, n-butyl, t-butyl, n-pentyl, phenyl, —CH$_2$OCH$_3$, —CH$_2$CN, —CH$_2$OCH$_2$CH$_2$CN, —CH$_2$C(CH$_3$)$_2$CH$_2$CH$_2$CN, —CH$_2$C(CH$_2$CH$_3$)$_2$CH$_2$CH$_2$CN, —CH$_2$CH$_2$CN, —CH$_2$N(CH$_2$CH$_2$CN)$_2$, —CH$_2$N(CH$_3$)CH$_2$CH$_2$CN, —CH(NH$_2$)CH$_2$CN, —CH$_2$Cl, —CH$_2$OH, —CH$_2$CH$_2$OH, —CH$_2$CH$_2$OH, —CH$_2$CH$_2$CH$_2$CH$_2$OH, —CH$_2$CH$_2$OC(O)CH$_3$, —CH$_2$CH$_2$OC(O)CH$_2$NH$_2$, —CH$_2$CH$_2$NHCH$_3$, —CH$_2$CH$_2$N(CH$_3$)$_2$, —CH$_2$N(CH$_2$CH$_3$)$_2$, —CH$_2$CH$_2$N(CH$_2$CH$_3$)$_2$, —CH$_2$CH$_2$CH$_2$N(CH$_3$)$_2$, —CH$_2$CH$_2$CH$_2$N$^+$(CH$_3$)$_3$, —CH$_2$OCH$_2$CH(CH$_3$)$_2$, —CH$_2$CH$_2$N(CH$_3$)C(O)OC(CH$_3$)$_3$, —CH$_2$N(CH$_2$CH$_2$CN)CH$_2$CH(CH$_3$)$_2$, —CH(CH$_2$CN)N(CH$_3$)$_2$, —CH$_2$CH(CH$_2$CN)NHC(O)OC(CH$_3$)$_3$,

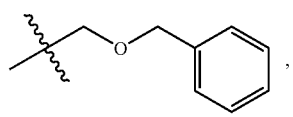

,

* * * * *